US009028562B2

(12) United States Patent
Lagrange et al.

(10) Patent No.: US 9,028,562 B2
(45) Date of Patent: May 12, 2015

(54) DYE COMPOSITION USING A 2-HYDROXYNAPHTHALENE, (ACYLAMINO)PHENOL OR QUINOLINE COUPLER IN A FATTY-SUBSTANCE-RICH MEDIUM, DYEING PROCESS AND DEVICE THEREFOR

(75) Inventors: Alain Lagrange, Coupvray (FR); Marie Mignon, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/113,862

(22) PCT Filed: Apr. 19, 2012

(86) PCT No.: PCT/EP2012/057179
§ 371 (c)(1),
(2), (4) Date: Oct. 25, 2013

(87) PCT Pub. No.: WO2012/146526
PCT Pub. Date: Nov. 1, 2012

(65) Prior Publication Data
US 2014/0041133 A1 Feb. 13, 2014

Related U.S. Application Data

(60) Provisional application No. 61/483,285, filed on May 6, 2011, provisional application No. 61/483,303, filed on May 6, 2011, provisional application No. 61/483,351, filed on May 6, 2011, provisional application No. 61/483,359, filed on May 6, 2011.

(30) Foreign Application Priority Data

Apr. 29, 2011 (FR) .................... 11 53688
Apr. 29, 2011 (FR) .................... 11 53690
Apr. 29, 2011 (FR) .................... 11 53701
Apr. 29, 2011 (FR) .................... 11 53702

(51) Int. Cl.
| | | |
|---|---|---|
| *A61Q 5/10* | (2006.01) | |
| *A61K 8/58* | (2006.01) | |
| *A61K 8/31* | (2006.01) | |
| *A61K 8/39* | (2006.01) | |
| *A61K 8/41* | (2006.01) | |
| *A61K 8/34* | (2006.01) | |
| *A61K 8/49* | (2006.01) | |
| *A61K 8/22* | (2006.01) | |
| *A61K 8/33* | (2006.01) | |
| *A61K 8/46* | (2006.01) | |

(52) U.S. Cl.
CPC ... *A61K 8/58* (2013.01); *A61K 8/31* (2013.01); *A61K 8/39* (2013.01); *A61K 8/41* (2013.01); *A61Q 5/10* (2013.01); *A61K 8/342* (2013.01); *A61K 8/347* (2013.01); *A61K 8/411* (2013.01); *A61K 8/415* (2013.01); *A61K 8/4926* (2013.01); *A61K 8/22* (2013.01); *A61K 8/33* (2013.01); *A61K 8/345* (2013.01); *A61K 8/46* (2013.01); *A61K 8/49* (2013.01); *A61K 8/4906* (2013.01); *A61K 8/492* (2013.01); *A61K 8/4946* (2013.01)

(58) Field of Classification Search
CPC ........... A61Q 5/10; A61K 8/31; A61K 8/342; A61K 8/347; A61K 8/492; A61K 8/4926; A61K 2800/88; C07D 221/02; C07D 215/00; C07D 217/00; C07C 39/04; C07C 39/06; C07C 39/14
USPC ................. 8/405, 406, 412; 546/171, 185
See application file for complete search history.

(56) References Cited

U.S. PATENT DOCUMENTS

| | | |
|---|---|---|
| 4,003,699 A | 1/1977 | Rose et al. |
| 4,137,180 A | 1/1979 | Naik et al. |
| RE30,199 E | 1/1980 | Rose et al. |
| 4,874,554 A | 10/1989 | Lange et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,766,576 A | 6/1998 | Löwe et al. |
| 6,099,592 A | 8/2000 | Vidal et al. |

(Continued)

FOREIGN PATENT DOCUMENTS

| | | |
|---|---|---|
| DE | 2359399 | 6/1975 |
| DE | 3843892 A1 | 6/1990 |

(Continued)

OTHER PUBLICATIONS

STIC Search Report dated Dec. 3, 2013.*

(Continued)

*Primary Examiner* — Eisa Elhilo
(74) *Attorney, Agent, or Firm* — The Marbury Law Group, PLLC

(57) ABSTRACT

The present invention relates to a cosmetic composition for dyeing keratin fibers, in particular human keratin fibers such as the hair, comprising: a) one or more fatty substances; b) one or more surfactants; c) one or more oxidation bases; d) one or more couplers based on 2-hydroxynaphthalene derivatives or particular phenol derivatives, acylaminophenol derivatives or quinoline derivatives; f) one or more basifying agents; e) optionally one or more chemical oxidizing agents; and the fatty substance content representing in total at least 25% by weight relative to the total weight of the formulation. The present invention also relates to a process using this composition, and to a multi-compartment device that is suitable for performing the said process.

27 Claims, No Drawings

(56) References Cited

U.S. PATENT DOCUMENTS

| | | |
|---|---|---|
| 6,284,003 B1 | 9/2001 | Rose et al. |
| 6,338,741 B1 | 1/2002 | Vidal et al. |
| 6,475,247 B1 * | 11/2002 | Vandenbossche et al. ........ 8/405 |
| 6,645,258 B2 | 11/2003 | Vidal et al. |
| 6,730,789 B1 | 5/2004 | Birault et al. |
| 7,306,631 B2 * | 12/2007 | Glenn et al. ...................... 8/405 |
| 7,918,903 B2 | 4/2011 | Audousset et al. |
| 7,927,380 B2 | 4/2011 | Audousset et al. |
| 7,927,382 B2 | 4/2011 | Audousset et al. |
| 7,927,383 B2 | 4/2011 | Hercouet et al. |
| 8,070,831 B2 | 12/2011 | Simonet et al. |
| 2002/0050013 A1 | 5/2002 | Vidal et al. |
| 2003/0019051 A9 | 1/2003 | Vidal et al. |
| 2005/0251927 A9 * | 11/2005 | Vidal et al. ...................... 8/405 |
| 2007/0044253 A1 | 3/2007 | Kravtchenko et al. |
| 2010/0154141 A1 | 6/2010 | Hercouet et al. |
| 2010/0162493 A1 | 7/2010 | Audousset et al. |
| 2010/0175203 A1 | 7/2010 | Audousset et al. |
| 2010/0180389 A1 | 7/2010 | Hercouet et al. |
| 2010/0247465 A1 | 9/2010 | Simonet et al. |
| 2011/0126362 A1 | 6/2011 | Kravtchenko et al. |

FOREIGN PATENT DOCUMENTS

| | | |
|---|---|---|
| DE | 4133957 A1 | 4/1993 |
| DE | 4316602 A1 | 11/1994 |
| DE | 19543988 A1 | 5/1997 |
| DE | 102008061864 A1 | 10/2010 |
| EP | 0770375 A1 | 5/1997 |
| EP | 1757328 A1 | 2/2007 |
| EP | 2198839 A1 | 6/2010 |
| EP | 2198840 A1 | 6/2010 |
| EP | 2198853 A1 | 6/2010 |
| EP | 2198927 A2 | 6/2010 |
| FR | 2733749 | 11/1996 |
| FR | 2788690 A1 | 7/2000 |
| FR | 2801308 | 5/2001 |
| FR | 2886136 A1 | 12/2006 |
| FR | 2946875 A1 | 12/2010 |
| GB | 1026978 | 4/1966 |
| GB | 1153196 | 5/1969 |
| JP | 0219576 | 1/1990 |
| JP | 05163124 | 6/1993 |
| JP | 2004026703 A | 1/2004 |
| WO | 9408969 | 4/1994 |
| WO | 9408970 | 4/1994 |
| WO | 9426241 | 11/1994 |
| WO | 9615765 | 5/1996 |
| WO | 2010070244 A2 | 6/2010 |

OTHER PUBLICATIONS

PCT/ISA/205 including partial Search Report for PCT/EP2012/057179, (2012).

Todd & Byers, "Volatile Silicone Fluids for Cosmetics," Cosmetics and Toiletries, vol. 91, Jan. 76, pp. 27-32.

Porter, M.R., "Handbook of Surfactants," published by Blackie & Son (Glasgow and London), 1991, pp. 116-178.

* cited by examiner

DYE COMPOSITION USING A 2-HYDROXYNAPHTHALENE, (ACYLAMINO)PHENOL OR QUINOLINE COUPLER IN A FATTY-SUBSTANCE-RICH MEDIUM, DYEING PROCESS AND DEVICE THEREFOR

CROSS REFERENCE TO RELATED APPLICATIONS

This is a national stage application of PCT/EP2012/057179, filed internationally on Apr. 19, 2012, which claims priority to U.S. Provisional Application Nos. 61/483,285; 61/483,303; 61/483,351 and 61/483,359, filed on May 6, 2011, as well as French Application Nos. FR1153688; FR1153690; FR1153701 and FR1153702, filed on Apr. 29, 2011, all of which are incorporated by reference herein in their entireties.

The present invention relates to a composition for dyeing keratin fibres, comprising a) one or more fatty substances and b) one or more surfactants, c) one or more oxidation bases and d) one or more couplers, including at least one coupler chosen from i) 2-hydroxynaphthalene derivatives, ii) particular phenol derivatives, iii) acylaminophenol derivatives, iv) quinoline derivatives; e) one or more basifying agents, f) optionally one or more chemical oxidizing agents, and the content of fatty substances in the composition representing in total at least 25% by weight relative to the total weight of the composition.

The present invention also relates to a dyeing process using this composition, and to a multi-compartment device that is suitable for using this composition.

Many people have sought for a long time to modify the colour of their hair and in particular to mask their grey hair.

One of the dyeing methods is "permanent" or oxidation dyeing, which uses dye compositions containing oxidation dye precursors, generally known as oxidation bases. These oxidation bases are colourless or weakly coloured compounds, which, when combined with oxidizing products, may give rise to coloured compounds by a process of oxidative condensation.

It is also known that the shades obtained with these oxidation bases may be varied by combining them with couplers or coloration modifiers, the latter being chosen especially from aromatic meta-diamines, meta-aminophenols, meta-diphenols and certain heterocyclic compounds such as indole compounds. The variety of molecules used as oxidation bases and couplers allows a wide range of colours to be obtained.

It is also possible to use direct dyes in order especially to afford tints on the coloration obtained. These direct dyes are coloured and colouring molecules that have affinity for fibres. Examples that may be mentioned include benzenic, anthraquinone, nitropyridine, azo, xanthene, acridine, azine and triarylmethane direct dyes.

Permanent dyeing processes thus consist in using, with the dye composition, an aqueous composition comprising at least one oxidizing agent, under alkaline pH conditions in the vast majority of cases. The role of this oxidizing agent is, at least partly, to degrade the melanin of the hair, which, depending on the nature of the oxidizing agent present, leads to more or less pronounced lightening of the fibres. The oxidizing agent used is generally hydrogen peroxide.

One of the difficulties encountered during the implementation of the dyeing processes of the prior art arises from the fact that they are implemented under alkaline conditions and that the basifying agents most commonly used are aqueous ammonia and amines. Specifically, the basifying agent makes it possible to adjust the pH of the composition to an alkaline pH to enable activation of the oxidizing agent. In addition, this basifying agent causes swelling of the keratin fibre, with raising of the scales, which promotes the penetration of the oxidizing agent, and also of the dyes, if they are present, essentially oxidation dyes, into the fibre, and thus increases the efficacy of the dyeing or lightening reaction.

However, these basifying agents, and especially aqueous ammonia, cause the user discomfort due to their strong characteristic odour.

Moreover, not only may the user be inconvenienced by the odour, but may also be confronted with greater risks of intolerance, for instance irritation of the scalp, which is especially reflected by stinging.

It is also important to obtain colorations that are light-fast. Now, the use of certain couplers, for instance meta-phenylenediamines, induces degradation by solar radiation.

Moreover, it has been proposed in standard oxidation dyeing to use naphthalene-based couplers in the presence of oxidation bases to produce relatively photostable shades, but, firstly, with couplers of this type, the intensity of coloration obtained on the head of hair (lengths, ends) is relatively poor, and, secondly, the covering of the roots is very mediocre.

One of the objects of the present invention is to propose compositions for dyeing human keratin fibres such as the hair that do not have the drawbacks of the existing compositions.

In particular, the composition according to the invention, in the presence of a chemical oxidizing agent, produces satisfactory colours especially in terms of coverage or colour build-up at the root of the hairs, which makes it possible to avoid a "root" effect of the coloration.

Colorations that are very light-stable may also be obtained.

Furthermore, the invention makes it possible to achieve substantial degrees of lightening while at the same time colouring, without using persalts or increasing the amount of chemical oxidizing agent or of basifying agent.

These aims and others are achieved by the present invention, one subject of which is thus a composition for dyeing keratin fibres, in particular human keratin fibres such as the hair, comprising:

a) one or more fatty substances;
b) one or more surfactants;
c) one or more oxidation bases;
d) one or more couplers chosen from the following derivatives:
   i) 2-hydroxynaphthalenes;
   ii) phenols of formula (B1) below:

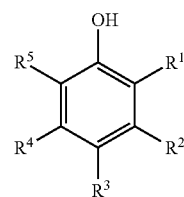

(B1)

and also salts thereof, optical and geometrical isomers and tautomers thereof, and hydrates thereof; in which formula (B1):

$R^1$, $R^2$, $R^3$, $R^4$ and $R^5$, which may be identical or different, represent:
a hydrogen atom;
a halogen atom;

an optionally substituted, linear or branched $C_1$-$C_8$ alkyl or $C_3$-$C_8$ alkenyl radical;

a group —SR or —OR in which R represents a hydrogen atom or an optionally substituted, linear or branched $C_1$-$C_8$ alkyl or $C_3$-$C_8$ alkenyl radical;

a ($C_1$-$C_4$)alkylcarbonyl group;

a hydrogenocarbonyl group (H—C(O)—);

a sulfonic acid group;

a group —NH—C(O)—R' or —NH—S(O)$_2$R' in which R' represents a hydrogen atom, an optionally substituted, linear or branched $C_1$-$C_8$ alkyl or $C_3$-$C_8$ alkenyl radical, or an optionally substituted phenyl group;

at least one of the radicals $R^1$, $R^3$ and $R^5$ representing a hydrogen atom;

two groups chosen from $R^1$, $R^2$, $R^3$, $R^4$ and $R^5$ and borne by adjacent carbon atoms may form, together with the said carbon atoms, an optionally substituted ring or heterocycle, optionally interrupted with one or more groups comprising at least one heteroatom, preferably chosen from an oxygen atom, a sulfur atom, a carbonyl group, a group —NR"— in which R" represents a hydrogen atom or a $C_1$-$C_4$ alkyl or ($C_1$-$C_4$)alkylcarbonyl radical;

formula (B1) containing only one group —NH—C(O)— and/or at least one group —NH—S(O)$_2$—, these groups being optionally engaged in a heterocycle;

iii) acylaminophenols and iv) quinolines;

e) one or more basifying agents;

f) optionally one or more chemical oxidizing agents; and the content of fatty substances representing in total at least 25% by weight relative to the total weight of the formulation.

A subject of the invention is also dyeing processes using the composition of the invention containing at least one chemical oxidizing agent, and a multi-compartment device for using the composition of the invention.

Thus, the use of the dye composition according to the invention especially in the presence of a chemical oxidizing agent leads to strong, chromatic and/or sparingly selective colorations, i.e. colorations that are uniform along the fibre. The dyeing process of the invention also makes it possible particularly to cover keratin fibres at their root, especially down to three centimeters from the base of the said fibres. Furthermore, the colours obtained after treating the fibres remain stable, in particular towards light.

The invention also makes it possible to reduce the amounts of active agents of the invention such as the dyes and/or basifying agents and/or oxidizing agents.

Moreover, the processes according to the invention use formulations that are less malodorous during their application to the hair or during their preparation.

Other characteristics and advantages of the invention will emerge more clearly on reading the description and the examples that follow.

In the text hereinbelow, unless otherwise indicated, the limits of a range of values are included in that range.

The human keratin fibres treated via the process according to the invention are preferably the hair.

The expression "at least one" is equivalent to the expression "one or more".

a) Fatty Substances

As has already been mentioned, the composition of the invention comprises a) one or more fatty substances.

The term "fatty substance" means an organic compound that is insoluble in water at ordinary temperature (25° C.) and at atmospheric pressure (760 mmHg) (solubility of less than 5%, preferably 1% and even more preferentially 0.1%). They have in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

Preferably, the fatty substances of the invention do not contain any salified or unsalified carboxylic acid groups (—C(O)OH or —C(O)O$^-$). Particularly, the fatty substances of the invention are neither polyoxyalkylenated nor polyglycerolated.

The term "oil" means a "fatty substance" that is liquid at room temperature (25° C.) and at atmospheric pressure (760 mmHg).

The term "non-silicone oil" means an oil not containing any silicon atoms (Si) and the term "silicone oil" means an oil containing at least one silicon atom.

More particularly, the fatty substance(s) are chosen from $C_6$-$C_{16}$ alkanes, nonsilicone oils of animal, plant, mineral or synthetic origin, fatty alcohols, esters of a fatty acid and/or of a fatty alcohol, nonsilicone waxes and silicones.

It is recalled that, for the purposes of the invention, fatty alcohols, esters and acids more particularly have at least one linear or branched, saturated or unsaturated hydrocarbon-based group comprising 6 to 30 carbon atoms, which is optionally substituted, in particular with one or more hydroxyl groups (in particular 1 to 4). If they are unsaturated, these compounds may have one to three conjugated or non-conjugated carbon-carbon double bonds.

As regards the $C_6$-$C_{16}$ alkanes, they are linear or branched, and possibly cyclic. Examples that may be mentioned include hexane, dodecane and isoparaffins such as isohexadecane and isodecane.

As oils of animal, plant, mineral or synthetic origin that may be used in the composition of the invention, examples that may be mentioned include:

hydrocarbon-based oils of animal origin, such as perhydrosqualene;

triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil.

linear or branched hydrocarbons of mineral or synthetic origin, containing more than 16 carbon atoms, such as liquid paraffins, petroleum jelly, liquid petroleum jelly, polydecenes, and hydrogenated polyisobutene such as Parleam®;

fluoro oils, for instance perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that are suitable for use in the invention are more particularly chosen from linear or branched, saturated or unsaturated alcohols comprising from 6 to 30 carbon atoms and preferably from 8 to 30 carbon atoms. Examples that may be mentioned include cetyl alcohol, stearyl alcohol and the mixture thereof (cetylstearyl alcohol), octyldodecanol, 2-butyloctanol, 2-hexyldecanol, 2-undecylpentadecanol, oleyl alcohol and linoleyl alcohol.

As regards the esters of a fatty acid and/or of a fatty alcohol, which are advantageously different than the triglycerides mentioned above, mention may be made especially of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of monocarboxylic, dicarboxylic or tricarboxylic acids and of $C_2$-$C_{26}$ dihydroxy, trihydroxy, tetrahydroxy or pentahydroxy alcohols may also be used.

Mention may be made especially of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$, and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

More particularly, use is made of monoesters and diesters and especially sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate.

Examples of esters or mixtures of esters of sugar and of fatty acid that may also be mentioned include:
  the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
  the products sold under the name Ryoto Sugar Esters, for example referenced B370 and corresponding to sucrose behenate formed from 20% monoester and 80% di-tri-ester-polyester;
  the sucrose mono-dipalmito-stearate sold by the company Goldschmidt under the name Tegosoft® PSE.

The nonsilicone wax(es) are chosen in particular from carnauba wax, candelilla wax, esparto wax, paraffin wax, ozokerite, plant waxes, such as olive tree wax, rice wax, hydrogenated jojoba wax or absolute flower waxes, such as the blackcurrant blossom essential wax sold by Bertin (France), or animal waxes, such as beeswaxes or modified beeswaxes (cerabellina); other waxes or waxy raw materials that may be used according to the invention are in particular marine waxes, such as that sold by Sophim under the reference M82, polyethylene waxes or polyolefin waxes in general.

The silicones that may be used in the cosmetic compositions of the present invention are volatile or nonvolatile, cyclic, linear or branched silicones, which are unmodified or modified with organic groups, having a viscosity from $5\times10^{-6}$ to 2.5 $m^2$/s at 25° C., and preferably $1\times10^{-5}$ to 1 $m^2$/s.

The silicones that may be used in accordance with the invention may be in the form of oils, waxes, resins or gums.

Preferably, the silicone is chosen from polydialkylsiloxanes, especially polydimethylsiloxanes (PDMS), and organomodified polysiloxanes comprising at least one functional group chosen from poly(oxyalkylene) groups, amino groups and alkoxy groups.

Organopolysiloxanes are defined in greater detail in Walter Noll's "Chemistry and Technology of Silicones" (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

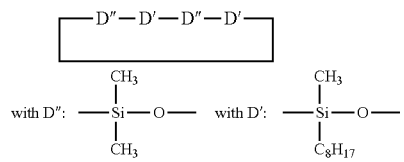

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*.

Non-volatile polydialkylsiloxanes, polydialkylsiloxane gums and resins, polyorganosiloxanes modified with the organofunctional groups above, and mixtures thereof, are preferably used.

These silicones are more particularly chosen from polydialkylsiloxanes, among which mention may be made mainly of polydimethylsiloxanes containing trimethylsilyl end groups. The viscosity of the silicones is measured at 25° C. according to ASTM standard 445 Appendix C.

Among these polydialkylsiloxanes, mention may be made, in a nonlimiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

The silicone gums that can be used in accordance with the invention are especially polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that can be used more particularly in accordance with the invention are mixtures such as:

mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;

mixtures formed from a polydimethylsiloxane gum and of a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;

mixtures of two PDMSs with different viscosities, and more particularly of a PDMS gum and a PDMS oil, such as the product SF 1236 from the company General Electric. The product SF 1236 is a mixture of a gum SE 30 defined above with a viscosity of 20 m$^2$/s and of an oil SF 96 with a viscosity of $5 \times 10^{-6}$ m$^2$/s. This product preferably comprises 15% of gum SE 30 and 85% of an oil SF 96.

The organopolysiloxane resins that may be used in accordance with the invention are crosslinked siloxane systems containing the following units:

$R_2SiO_{2/2}$, $R_3SiO_{1/2}$, $RSiO_{3/2}$ and $SiO_{4/2}$ in which R represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, which are silicones of dimethyl/trimethylsiloxane structure.

Mention may also be made of the trimethyl siloxysilicate type resins sold in particular under the names X22-4914, X21-5034 and X21-5037 by the company Shin-Etsu.

The organomodified silicones that can be used in accordance with the invention are silicones as defined above and comprising in their structure one or more organofunctional groups attached via a hydrocarbon-based group.

Besides the silicones described above, the organomodified silicones may be polydiarylsiloxanes, especially polydiphenylsiloxanes, and polyalkylarylsiloxanes functionalized with the organofunctional groups mentioned previously.

The polyalkylarylsiloxanes are chosen particularly from linear and/or branched polydimethyl/methylphenylsiloxanes and polydimethyl/diphenylsiloxanes with a viscosity of from $1 \times 10^{-5}$ to $5 \times 10^{-2}$ m$^2$/s at 25° C.

Among these polyalkylarylsiloxanes, examples that may be mentioned include the products sold under the following names:

the Silbione® oils of the 70 641 series from Rhodia;
the oils of the series Rhodorsil® 70 633 and 763 from Rhodia;
the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Among the organomodified silicones, mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils Silwet® L 722, L 7500, L 77 and L 711 by the company Union Carbide, and the ($C_{12}$)alkylmethicone copolyol sold by the company Dow Corning under the name Q2 5200;

substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, in particular, $C_1$-$C_4$ aminoalkyl groups;

alkoxy groups such as the product sold under the name Silicone Copolymer F-755 by SWS Silicones, and Abil Wax® 2428, 2434 and 2440 by the company Goldschmidt.

Preferably, the fatty substance(s) do not comprise any $C_2$-$C_3$ oxyalkylene units or any glycerolated units.

More particularly, the fatty substances are chosen from compounds that are liquid or pasty at room temperature (25° C.) and at atmospheric pressure.

Preferably, the fatty substance is a compound that is liquid at a temperature of 25° C. and at atmospheric pressure.

The fatty substance(s) are advantageously chosen from $C_6$-$C_{16}$ alkanes, nonsilicone oils of plant, mineral or synthetic origin, fatty alcohols, esters of a fatty acid and/or of a fatty alcohol, and silicones, or mixtures thereof.

Preferably, the fatty substance(s) are chosen from liquid petroleum jelly, $C_6$-$C_{16}$ alkanes, polydecenes, liquid esters of fatty acids and/or of fatty alcohols, and liquid fatty alcohols, or mixtures thereof.

Better still, the fatty substance(s) are chosen from liquid petroleum jelly, $C_6$-$C_{16}$ alkanes and polydecenes.

The composition according to the invention comprises at least 25% by weight of fatty substance.

The composition according to the invention more particularly has a fatty substance content ranging from 25% to 80% by weight, preferably from 30% to 70% by weight and even more advantageously from 30% to 60% by weight relative to the weight of the composition.

b) Surfactants

The composition of the invention also comprises b) one or more surfactants.

In particular, the surfactant(s) are chosen from anionic, amphoteric, zwitterionic, cationic and nonionic surfactants, and preferentially nonionic surfactants.

The term "anionic surfactant" means a surfactant comprising, as ionic or ionizable groups, only anionic groups. These anionic groups are preferably chosen from the groups —C(O)OH, —C(O)O⁻, —SO₃H, —S(O)₂O⁻, —OS(O)₂OH, —OS(O)₂O⁻, —P(O)OH₂, —P(O)₂O⁻, —P(O)O₂, —P(OH)₂, =P(O)OH, —P(OH)O⁻, =P(O)O⁻, =POH, =PO⁻, the anionic parts comprising a cationic counterion such as an alkali metal, an alkaline-earth metal or an ammonium.

Mention may be made, as examples of anionic surfactants that may be used in the composition according to the invention, of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglycoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 24 carbon atoms and the aryl group denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids can be selected from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, the ammonium salts, the amine salts and in particular amino alcohol salts or the alkaline-earth metal salts such as the magnesium salts.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Among the anionic surfactants mentioned, use is preferably made of ($C_6$-$C_{24}$)alkyl sulfates, ($C_6$-$C_{24}$)alkyl ether sulfates comprising from 2 to 50 ethylene oxide units, especially in the form of alkali metal, ammonium, amino alcohol and alkaline-earth metal salts, or a mixture of these compounds.

It is particularly preferred to use ($C_{12}$-$C_{20}$)alkyl sulfates, ($C_{12}$-$C_{20}$)alkyl ether sulfates comprising from 2 to 20 ethylene oxide units, especially in the form of alkali metal, ammonium, amino alcohol and alkaline-earth metal salts, or a mixture of these compounds. Better still, use is made of sodium lauryl ether sulfate containing 2.2 mol of ethylene oxide.

The amphoteric or zwitterionic surfactant(s), which are preferably nonsilicone, that may be used in the present invention may especially be derivatives of optionally quaternized aliphatic secondary or tertiary amines, in which derivatives the aliphatic group is a linear or branched chain comprising from 8 to 22 carbon atoms, said amine derivatives containing at least one anionic group, for instance a carboxylate, sulfonate, sulfate, phosphate or phosphonate group. Mention may be made in particular of ($C_8$-$C_{20}$)alkylbetaines, sulfobetaines, ($C_8$-$C_{20}$)alkylamido($C_3$-$C_8$)alkylbetaines and ($C_8$-$C_{20}$)alkylamido($C_6$-$C_8$)alkylsulfobetaines.

Among the optionally quaternized secondary or tertiary aliphatic amine derivatives that may be used, as defined above, mention may also be made of the compounds of respective structures (A1) and (A2) below:

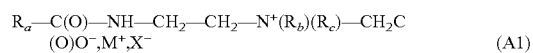

in which formula (A1):

$R_1$ represents a $C_{10}$-$C_{30}$ alkyl or alkenyl group derived from an acid $R_a$COOH preferably present in hydrolysed coconut oil, or a heptyl, nonyl or undecyl group;

$R_b$ represents a β-hydroxyethyl group; and $R_c$ represents a carboxymethyl group;

$M^+$ represents a cationic counterion derived from an alkali metal or alkaline-earth metal, such as sodium, an ammonium ion or an ion derived from an organic amine, and $X^-$ represents an organic or inorganic anionic counterion, such as that chosen from halides, acetates, phosphates, nitrates, $(C_1-C_4)$alkyl sulfates, $(C_1-C_4)$alkyl- or $(C_1-C_4)$alkylarylsulfonates, in particular methyl sulfate and ethyl sulfate; or alternatively $M^+$ and $X^-$ are absent;

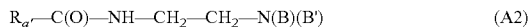

$$R_a\text{—}C(O)\text{—}NH\text{—}CH_2\text{—}CH_2\text{—}N(B)(B') \quad (A2)$$

in which formula (A2):

B represents the group —$CH_2$—$CH_2$—O—X′;

B′ represents the group —$(CH_2)_z$Y′, with z=1 or 2;

X′ represents the group —$CH_2$—C(O)OH, —$CH_2$—C(O)OZ′, —$CH_2$—$CH_2$—C(O)OH, —$CH_2$—$CH_2$—C(O)OZ′, or a hydrogen atom;

Y′ represents the group —C(O)OH, —C(O)OZ′, —$CH_2$—CH(OH)—$SO_3$H or the group —$CH_2$—CH(OH)—$SO_3$—Z′;

Z′ represents a cationic counterion derived from an alkali metal or alkaline-earth metal, such as sodium, an ammonium ion or an ion derived from an organic amine;

$R_a$, represents a $C_{10}$-$C_{30}$ alkyl or alkenyl group of an acid $R_a$—C(O)OH preferably present in coconut oil or in hydrolyzed linseed oil, an alkyl group, especially of $C_{17}$ and its iso form, or an unsaturated $C_{17}$ group.

These compounds are classified in the CTFA dictionary, 5th edition, 1993, under the names disodium cocoamphodiacetate, disodium lauroampho-diacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Among the amphoteric or zwitterionic surfactants mentioned above, use is preferably made of $(C_8$-$C_{20})$alkylbetaines such as cocoylbetaine, and $(C_8$-$C_{20})$alkylamido$(C_3$-$C_8)$alkylbetaines such as cocamidopropylbetaine, and mixtures thereof. More preferentially, the amphoteric or zwitterionic surfactant(s) are chosen from cocamidopropylbetaine and cocoylbetaine.

The cationic surfactant(s) that can be used in the compositions of the present invention comprise, for example, salts of optionally polyoxyalkylenated primary, secondary or tertiary fatty amines, quaternary ammonium salts, and mixtures thereof.

Examples of quaternary ammonium salts that may especially be mentioned include:

those corresponding to the general formula (A4) below:

in which formula (A4):

$R_8$ to $R_{11}$, which may be identical or different, represent a linear or branched aliphatic group comprising from 1 to 30 carbon atoms, or an aromatic group such as aryl or alkylaryl, it being understood that at least one of the groups $R_8$ to $R_{11}$ comprises from 8 to 30 carbon atoms and preferably from 12 to 24 carbon atoms; and $X^-$ represents an organic or inorganic anionic counterion, such as that chosen from halides, acetates, phosphates, nitrates, $(C_1-C_4)$alkyl sulfates, $(C_1-C_4)$alkyl- or $(C_1-C_4)$alkylarylsulfonates, in particular methyl sulfate and ethyl sulfate.

The aliphatic groups of $R_8$ to $R_{11}$ may also comprise heteroatoms especially such as oxygen, nitrogen, sulfur and halogens.

The aliphatic groups of $R_8$ to $R_{11}$ are chosen, for example, from $C_1$-$C_{30}$ alkyl, $C_1$-$C_{30}$ alkoxy, polyoxy$(C_2$-$C_6)$alkylene, $C_1$-$C_{30}$ alkylamide, $(C_{12}$-$C_{22})$alkylamido$(C_2$-$C_6)$alkyl, $(C_{12}$-$C_{22})$alkylacetate, $C_1$-$C_{30}$ hydroxyalkyl, $X^-$ is an anionic counterion chosen from halides, phosphates, acetates, lactates, $(C_1$-$C_4)$alkyl sulfates, and $(C_1$-$C_4)$alkyl- or $(C_1$-$C_4)$alkylarylsulfonates.

Among the quaternary ammonium salts of formula (A4), preference is given firstly to tetraalkylammonium chlorides, for instance dialkyldimethylammonium or alkyltrimethylammonium chlorides in which the alkyl group contains approximately from 12 to 22 carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulfate, dipalmitoylethylhydroxyethylammonium methosulfate or distearoylethylhydroxyethylammonium methosulfate, or else, lastly, palmitylamidopropyltrimethylammonium chloride or stearamidopropyldimethyl(myristyl acetate)ammonium chloride, sold under the name Ceraphyl® 70 by the company Van Dyk;

quaternary ammonium salts of imidazoline, for instance those of formula (A5) below:

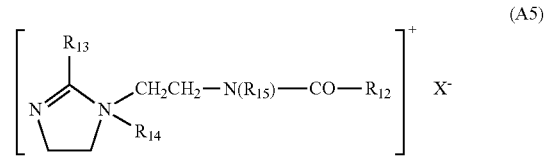

in which formula (A5):

$R_{12}$ represents an alkenyl or alkyl group comprising from 8 to 30 carbon atoms, for example fatty acid derivatives of tallow;

$R_{13}$ represents a hydrogen atom, a $C_1$-$C_4$ alkyl group or an alkenyl or alkyl group comprising from 8 to 30 carbon atoms;

$R_{14}$ represents a $C_1$-$C_4$ alkyl group;

$R_{15}$ represents a hydrogen atom or a $C_1$-$C_4$ alkyl group;

$X^-$ represents an organic or inorganic anionic counterion, such as that chosen from halides, phosphates, acetates, lactates, $(C_1$-$C_4)$alkyl sulfates, $(C_1$-$C_4)$alkyl- or $(C_1$-$C_4)$alkylarylsulfonates.

$R_{12}$ and $R_{13}$ preferably denote a mixture of alkenyl or alkyl groups comprising from 12 to 21 carbon atoms, for example tallow fatty acid derivatives, $R_{14}$ denotes a methyl group, and $R_{15}$ denotes a hydrogen atom. Such a product is sold, for example, under the name Rewoquat® W 75 by the company Rewo;

quaternary diammonium or triammonium salts, particularly of formula (A6) below:

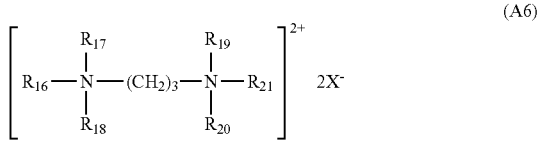

(A6)

in which formula (A6):

$R_{16}$ denotes an alkyl group comprising from about 16 to 30 carbon atoms, which is optionally hydroxylated and/or interrupted with one or more oxygen atoms;

$R_{17}$ is chosen from hydrogen, an alkyl group comprising from 1 to 4 carbon atoms or a group $—(CH_2)_3—N^+(R_{16a})(R_{17a})(R_{18a}), X^-$;

$R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms; and $X^-$, which may be identical or different, represents an organic or inorganic anionic counterion, such as that chosen from halides, acetates, phosphates, nitrates, $(C_1-C_4)$alkyl sulfates, $(C_1-C_4)$alkyl- or $(C_1-C_4)$alkylarylsulfonates, in particular methyl sulfate and ethyl sulfate.

Such compounds are, for example, Finquat CT-P, sold by the company Finetex (Quaternium 89), and Finquat CT, sold by the company Finetex (Quaternium 75);

quaternary ammonium salts containing one or more ester functions, such as those of formula (A7) below:

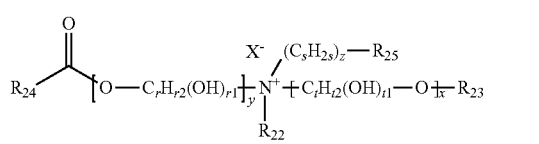

(A7)

in which formula (A7):

$R_{22}$ is chosen from $C_1-C_6$ alkyl and $C_1-C_6$ hydroxyalkyl or dihydroxyalkyl groups;

$R_{23}$ is chosen from:
the group

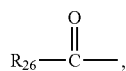, linear or branched, saturated or unsaturated $C_1-C_{22}$ hydrocarbon-based groups $R_{27}$,
a hydrogen atom;

$R_{25}$ is chosen from:
the group

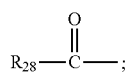;

linear or branched, saturated or unsaturated $C_1-C_6$ hydrocarbon-based groups $R_{29}$,
a hydrogen atom;

$R_{24}$, $R_{26}$ and $R_{28}$, which may be identical or different, are chosen from linear or branched, saturated or unsaturated $C_7-C_{21}$ hydrocarbon-based groups;

r, s and t, which may be identical or different, are integers ranging from 2 to 6;

r1 and t1, which may be identical or different, are equal to 0 or 1, with r2+r1=2r and t1+t2=2t y is an integer ranging from 1 to 10;

x and z, which may be identical or different, are integers ranging from 0 to 10;

$X^-$ represents an organic or inorganic anionic counterion; with the proviso that the sum x+y+z is from 1 to 15, that when x is 0 then $R_{23}$ denotes $R_{27}$, and that when z is 0 then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and may contain from 12 to 22 carbon atoms, or may be short and may contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}-C_{21}$ hydrocarbon-based groups, and more particularly from linear or branched, saturated or unsaturated $C_{11}-C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anionic counterion $X^-$ is preferably a halide, such as chloride, bromide or iodide; a $(C_1-C_4)$alkyl sulfate or a $(C_1-C_4)$alkyl- or $(C_1-C_4)$alkylaryl-sulfonate. However, it is possible to use methanesulfonate, phosphate, nitrate, tosylate, an anion derived from an organic acid, such as acetate or lactate, or any other anion that is compatible with the ammonium containing an ester function.

The anionic counterion $X^-$ is even more particularly chloride, methyl sulfate or ethyl sulfate.

Use is made more particularly in the composition according to the invention of the ammonium salts of formula (A7) in which:

$R_{22}$ denotes a methyl or ethyl group,
x and y are equal to 1,
z is equal to 0 or 1,
r, s and t are equal to 2,
$R_{23}$ is chosen from:
the group

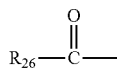

methyl, ethyl or $C_{14}-C_{22}$ hydrocarbon-based groups,
a hydrogen atom,
$R_{25}$ is chosen from:
the group

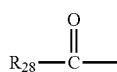

a hydrogen atom,
$R_{24}$, $R_{26}$ and $R_{28}$, which may be identical or different, are chosen from linear or branched, saturated or unsaturated $C_{13}$-$C_{17}$ hydrocarbon-based groups, and more particularly from linear or branched, saturated or unsaturated $C_{13}$-$C_{17}$ alkyl and alkenyl groups.

Advantageously, the hydrocarbon-based radicals are linear.

Among the compounds of formula (A7), examples that may be mentioned include salts, especially the chloride or methyl sulfate, of diacyloxy-ethyldimethylammonium, diacyloxyethylhydroxyethylmethylammonium, monoacyloxyethyldihydroxyethylmethylammonium, triacyloxyethylmethyl-ammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably methyl or ethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium salts of mono-, di- and triesters with a weight majority of diester salts.

It is also possible to use the ammonium salts containing at least one ester function that are described in U.S. Pat. No. 4,874,554 and U.S. Pat. No. 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the cationic surfactants that may be present in the composition according to the invention, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

Examples of nonionic surfactants that may be used in the composition used according to the invention are described, for example, in the *Handbook of Surfactants* by M. R. Porter, published by Blackie & Son (Glasgow and London), 1991, pp. 116-178. They are especially chosen from polyethoxylated, polypropoxylated and/or polyglycerolated alcohols, α-diols and ($C_1$-$C_{20}$)alkylphenols, containing at least one fatty chain comprising, for example, from 8 to 18 carbon atoms, the number of ethylene oxide and/or propylene oxide groups possibly ranging especially from 2 to 50, and the number of glycerol groups possibly ranging especially from 2 to 30.

Mention may also be made of copolymers of ethylene oxide and propylene oxide, optionally oxyethylenated fatty acid esters of sorbitan, fatty acid esters of sucrose, polyoxyalkylenated fatty acid esters, optionally oxyalkylenated alkylpolyglycosides, alkylglucoside esters, derivatives of N-alkylglucamine and of N-acylmethylglucamine, aldobionamides and amine oxides.

The nonionic surfactants are more particularly chosen from monooxyalkylenated or polyoxyalkylenated, monoglycerolated or polyglycerolated nonionic surfactants. The oxyalkylene units are more particularly oxyethylene or oxypropylene units, or a combination thereof, preferably oxyethylene units.

Examples of oxyalkylenated nonionic surfactants that may be mentioned include
  oxyalkylenated ($C_8$-$C_{24}$)alkylphenols;
  saturated or unsaturated, linear or branched, oxyalkylenated $C_8$-$C_{30}$ alcohols;
  saturated or unsaturated, linear or branched, oxyalkylenated $C_8$-$C_{30}$ amides;
  esters of saturated or unsaturated, linear or branched $C_8$-$C_{30}$ acids and of polyethylene glycols;
  polyoxyethylenated esters of saturated or unsaturated, linear or branched $C_8$-$C_{30}$ acids and of sorbitol;
  saturated or unsaturated, oxyethylenated plant oils;
  condensates of ethylene oxide and/or of propylene oxide, inter alia, alone or as mixtures;
  oxyethylenated and/or oxypropylenated silicones.

The surfactants contain a number of moles of ethylene oxide and/or of propylene oxide of between 1 and 100, preferably between 2 and 50 and preferably between 2 and 30. Advantageously, the nonionic surfactants do not comprise any oxypropylene units.

In accordance with one preferred embodiment of the invention, the oxyalkylenated nonionic surfactants are chosen from oxyethylenated $C_8$-$C_{30}$ alcohols comprising from 1 to 100 mol of ethylene oxide; polyoxyethylenated esters of linear or branched, saturated or unsaturated $C_8$-$C_{30}$ acids and of sorbitol comprising from 1 to 100 mol of ethylene oxide.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the formula (A8) below:

$$R_{29}O-[CH_2-CH(CH_2OH)-O]_m-H \qquad (A8)$$

in which formula (A8):
  $R_{29}$ represents a linear or branched $C_8$-$C_{40}$ and preferably $C_8$-$C_{30}$ alkyl or alkenyl radical; and
  m represents a number ranging from 1 to 30 and preferably from 1 to 10.

As examples of compounds of formula (A8) that are suitable for use in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol of formula (A8) may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the $C_8$/$C_{10}$ alcohol containing 1 mol of glycerol, the $C_{10}/C_{12}$ alcohol containing 1 mol of glycerol and the $C_{12}$ alcohol containing 1.5 mol of glycerol.

Preferably, the surfactant used in the process of the invention in the composition is a monooxyalkylenated or polyoxyalkylenated, particularly monooxyethylenated or polyoxyethylenated, or monooxypropylenated or polyoxypropylenated, nonionic surfactant, or a combination thereof, more particularly monooxyethylenated or polyoxyethylenated.

Preferably, the surfactant(s) are chosen from nonionic surfactants and anionic surfactants. More particularly, the surfactant(s) present in the composition are chosen from nonionic surfactants.

Even more preferentially, the nonionic surfactants are chosen from polyoxyethylenated sorbitol esters and polyoxyethylenated fatty alcohols, and mixtures thereof.

In the composition of the invention, the amount of surfactant(s) in the composition preferably ranges from 0.1% to 50% by weight and better still from 0.5% to 20% by weight relative to the total weight of the composition.

c) Oxidation Bases:

The composition of the invention comprises c) one or more oxidation bases chosen especially from heterocyclic bases and benzene-based bases, and the addition salts thereof.

The oxidation bases according to the invention are particularly chosen from from para-phenylenediamines, bis(phenyl)alkylenediamines, para-aminophenols and ortho-aminophenols, and the addition salts thereof.

Among the para-phenylenediamines that may be mentioned, for example, are para-phenylenediamine, para-toluenediamine, 2-chloro-para-phenylene-diamine, 2,3-dimethyl-para-phenylenediamine, 2,6-dimethyl-para-phenylene-diamine, 2,6-diethyl-para-phenylenediamine, 2,5-dimethyl-para-phenylene-diamine, N,N-dimethyl-para-phenylenediamine, N,N-diethyl-para-phenylene-diamine, N,N-dipropyl-para-phenylenediamine, 4-amino-N,N-diethyl-3-methyl-aniline, N,N-bis(β-hydroxyethyl)-para-phenylenediamine, 4-N,N-bis(β-hydroxy-ethyl)amino-2-methylaniline, 4-N,N-bis(β-hydroxyethyl)amino-2-chloroaniline, 2-p-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylene-diamine, N,N-(ethyl-β-hydroxyethyl)-para-phenylenediamine, N-(β,γ-dihydroxy-propyl)para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the addition salts thereof with an acid.

Among the para-phenylenediamines mentioned above, para-phenylene-diamine, para-toluenediamine, 2-isopropyl-para-phenylenediamine, 2-β-hydroxy-ethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylene-diamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis (4'-aminophenyl)-1,3-diamino-propanol, N,N'-bis-(β-hydroxyethyl)-N,N'-bis(4'-aminophenyl)ethylenediamine, N,N'-bis(4-aminophenyl)tetramethylenediamine, N,N'-bis (β-hydroxyethyl)-N,N'-bis(4-aminophenyl)tetramethylenediamine, N,N'-bis(4-methylaminophenyl)-tetramethylenediamine, N,N'-bis(ethyl)-N,N'-bis(4'-amino-3'-methylphenyl)-ethylenediamine, 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

The heterocyclic bases according to the invention are more particularly chosen from pyridine derivatives, pyrimidine derivatives and pyrazole derivatives, and the addition salts thereof.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the dyeing process according to the present invention are the 3-aminopyrazolo[1,5-a]pyridine oxidation bases or addition salts thereof described, for example, in patent application FR 2801308. Examples that may be mentioned include pyrazolo [1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo [1,5-a]pyridine-3,5-diamine, 5-morpholin-4-ylpyrazolo[1,5-a]pyrid-3-ylamine, 2-[(3-aminopyrazolo[1,5-a]pyrid-5-yl) (2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in patents DE 2359399; JP 88-169571; JP 05-63124; EP 0770375 or patent application WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)-pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. 4,5-Diamino-1-(β-methoxyethyl)-pyrazole may also be used.

A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

2,3-Diamino-6,7-dihydro-1H,5H-pyrazolo[1,2-a]pyrazol-1-one and/or a salt thereof will preferably be used.

4,5-Diamino-1-(β-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

The oxidation base(s) according to the invention each advantageously represent from 0.0001% to 10% by weight relative to the total weight of the composition, and preferably from 0.005% to 5% by weight relative to the total weight of the composition.

d) Couplers Based on i) 2-Hydroxynaphthalene Derivatives, ii) Phenol Derivatives of Formula (B1), iii) Acylaminophenols and iv) Quinoline Derivatives:

According to one particular embodiment of the invention, the cosmetic composition according to the invention comprises as coupler(s) as defined previously i) one or more 2-hydroxynaphthalene couplers.

The term "2-hydroxynaphthalene couplers" means couplers comprising a 2-hydroxynaphthalene unit, in which the hydroxyl group in position 2 is free or blocked with a hydrolysable function. Among the 2-hydroxynaphthalene couplers, mention may be made of those of formula (B4) and also salts thereof, optical or geometrical isomers and tautomers thereof, and hydrates thereof:

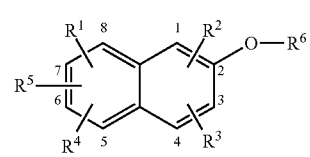

(B4)

in which formula (B4):

$R^1$, $R^2$, $R^3$, $R^4$ and $R^5$, which may be identical or different, represent an atom or a group chosen from:
i) hydrogen;
ii) halogen such as chlorine or bromine;
iii) hydroxyl;
iv) $NR^aR^b$ with $R^a$ and $R^b$, which may be identical or different, representing a hydrogen atom or a ($C_1$-$C_8$) alkyl group optionally substituted with a hydroxyl group or a (di)($C_1$-$C_8$)(alkyl)amino group;
or alternatively $R^a$ and $R^b$, with the nitrogen atom, together form a saturated or partially unsaturated mono- or polycyclic 3- to 10-membered heterocycle containing from 1 to 5 heteroatoms chosen from oxygen, nitrogen, sulfur, sulfoxide S(O) and sulfone $S(O)_2$, the heterocycle possibly being substituted with a group ($C_1$-$C_4$)alkyl or an oxo group; in particular, the heterocycle is chosen from morpholino, piperidino and piperazino;
v) ($C_1$-$C_8$)alkyl optionally substituted with one or more atoms or groups chosen from halogen such as fluorine, hydroxyl, cyano, carboxyl and amino $NR^aR^b$ as defined previously;
vi) ($C_1$-$C_8$)alkoxy;
vii) ($C_1$-$C_8$)alkyl-$S(O)_p$— with p=0, 1 or 2;
viii) aryl such as phenyl;
ix) saturated or partially unsaturated mono- or polycyclic 3- to 10-membered heterocycle containing from 1 to 5 heteroatoms chosen from oxygen, nitrogen, sulfur, sulfoxide S(O) and sulfone $S(O)_2$, the heterocycle possibly being substituted with a group ($C_1$-$C_4$)alkyl or an oxo group; in particular, the heterocycle is chosen from morpholinyl, piperidinyl and piperazinyl;
x) aryloxy such as phenoxy;
xi) cyano —CN;
xii) carboxyl-C(O)OM with M representing a hydrogen atom, a group ($C_1$-$C_8$)alkyl or a cation derived from an alkali metal, an alkaline-earth metal or an organic cation such as ammonium;
xiii) —$S(O)(OM)_2$ or —O—$S(O)(OM)_2$ with M as defined previously;
xiv) —C(O)$NR^aR^b$ or —$NR^a$—C(O)$R^b$ with $R^a$ and $R^b$ as defined previously;
xv) —$S(O)_n$—$NR^aR^b$ or —$NR^a$—$S(O)_n$—$R^b$ with n being equal to 1 or 2 and $R^a$ and $R^b$ as defined previously;
or alternatively two contiguous radicals $R^2$ and $R^3$ and/or $R^1$ and $R^5$ and/or $R^4$ and $R^5$ form, together with the carbon atom to which each is attached, an optionally substituted (hetero)cycle or (hetero) aryl; together preferentially form a benzo group;

$R^6$ represents a hydrogen atom, a hydrolysable protecting group for the hydroxyl group such as —C(X)—$R^7$ with X denoting an oxygen or sulfur atom, particularly oxygen, and $R^7$ denoting a hydrogen atom or a group ($C_1$-$C_8$)alkyl; $R^6$ preferentially represents a hydrogen atom.

According to one particular embodiment of the invention, the 2-hydroxynaphthalene coupler(s) of formula (B4) are such that $R^1$, $R^2$, $R^3$, $R^4$ and $R^5$, which may be identical or different, represent a hydrogen atom, a halogen atom such as bromine preferentially in position 1 or 3, a hydroxyl group preferentially in position 3 or 7, a cyano group preferentially in position 6, or a group $(C_1\text{-}C_8)$alkoxy preferentially in position 3, 4, 6 or 7.

More particularly, the 2-hydroxynaphthalene coupler(s) of formula (B4) are such that:

$R^1$ represents a group $(C_1\text{-}C_6)$alkyloxy such as methoxy, preferably in position 6 or 7; and $R^2$, $R^3$, $R^4$ and $R^5$ represent a hydrogen atom; or alternatively $R^3$ represents a group $(C_1\text{-}C_6)$alkyloxy such as methoxy, preferably in position 3 or 4; and $R^1$, $R^2$, $R^4$ and $R^5$ represent a hydrogen atom; or alternatively $R^3$ represents a halogen atom such as bromine, preferably in position 1 or 2; and $R^1$, $R^2$, $R^4$ and $R^5$ represent a hydrogen atom; or alternatively $R^4$ represents a cyano group, preferably in position 4; and $R^1$, $R^2$, $R^3$ and $R^5$ represent a hydrogen atom; or alternatively $R^1$, $R^2$, $R^3$, $R^4$ and $R^5$ represent a hydrogen atom.

As examples of 2-hydroxynaphthalene couplers according to the invention, mention may be made of the following compounds:

(1)
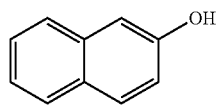
2-naphthol (2)
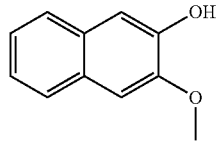
3-methoxy-2-naphthol (3)
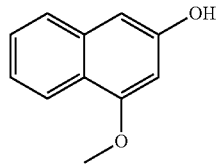
4-methoxy-2-naphthol (4)
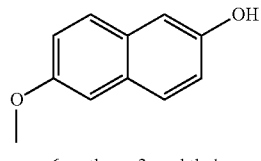
6-methoxy-2-naphthol (5)
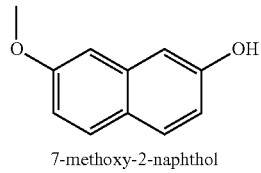
7-methoxy-2-naphthol -continued (6)
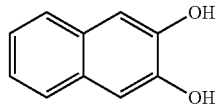
2,3-dihydroxynaphthalene (7)
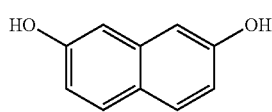
2,7-dihydroxynaphthalene (8)
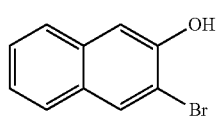
3-bromo-2-naphthol (9)
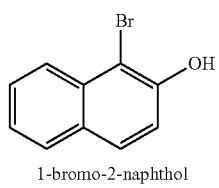
1-bromo-2-naphthol

(10)
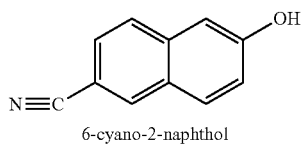
6-cyano-2-naphthol

According to one particular embodiment of the invention, the coupler(s) d) included in the composition are chosen from ii) the particular phenol-based couplers of formula (B1).

As indicated previously, these coupler(s) are chosen from those of formula (B1) and also salts thereof, optical or geometrical isomers and tautomers thereof, and hydrates thereof;

(B1)
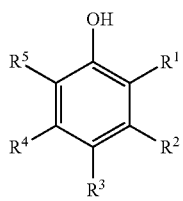

in which formula (B1):

$R^1$, $R^2$, $R^3$, $R^4$ and $R^5$, which may be identical or different, represent:
 a hydrogen atom;
 a halogen atom;
 an optionally substituted, linear or branched $C_1\text{-}C_8$ alkyl or $C_3\text{-}C_8$ alkenyl radical;
 a group —SR or —OR in which R represents a hydrogen atom or an optionally substituted, linear or branched $C_1\text{-}C_8$ alkyl or $C_3\text{-}C_8$ alkenyl radical;
 a $(C_1\text{-}C_4)$alkylcarbonyl group;
 a hydrogenocarbonyl group (H—C(O)—);
 a sulfonic acid group;
 a group —NH—C(O)—R' or —NH—S(O)$_2$R' in which R' represents a hydrogen atom, a linear or branched, optionally substituted $C_1$-$C_8$ alkyl or $C_3$-$C_8$ alkenyl radical, or an optionally substituted phenyl group;

at least one of the radicals $R^1$, $R^3$ and $R^5$ representing a hydrogen atom;

two groups chosen from $R^1$, $R^2$, $R^3$, $R^4$ and $R^5$ and borne by adjacent carbon atoms may form, together with the said carbon atoms, an optionally substituted ring or heterocycle, optionally interrupted with one or more groups comprising at least one heteroatom, preferably chosen from an oxygen atom, a sulfur atom, a carbonyl group, a group —NR"— in which R" represents a hydrogen atom or a $C_1$-$C_4$ alkyl or ($C_1$-$C_4$)alkylcarbonyl radical;

formula (B1) containing only one group —NH—C(O)— and/or at least one group —NH—S(O)$_2$—, these groups being optionally engaged in a heterocycle.

A "heterocyclic radical" is a fused or non-fused, monocyclic or polycyclic, non-aromatic radical containing 5 to 22 members and containing 1 to 6 heteroatoms selected from nitrogen, oxygen and sulphur atoms.

According to the invention, and unless otherwise specified, a linear or branched alkyl or alkenyl radical is said to be substituted when it bears one or more groups chosen from the following groups:
hydroxyl,
$C_1$-$C_4$ alkoxy,
amino,
mono- or di-($C_1$-$C_4$)alkylamino optionally substituted with one or more hydroxyl or amino groups,
tri($C_1$-$C_4$)alkylammonium,
carboxyl.

When the group is cyclic or heterocyclic, aromatic or non-aromatic, this group is said to be substituted when it bears one or more groups such as those mentioned above for the alkyl or alkenyl groups, and also with one or more $C_1$-$C_4$ alkyl radicals.

According to one preferred variant of the invention, the coupler(s) of amidophenol or sulfonamidophenol type of formula (B1) are chosen from those in which:

$R^1$, $R^2$, $R^3$, $R^4$ and $R^5$, which may be identical or different, represent:
a hydrogen atom;
a chlorine atom;
a linear or branched $C_1$-$C_8$ alkyl or $C_3$-$C_8$ alkenyl radical, optionally substituted with one or more hydroxyl, amino or carboxyl groups; and preferably a $C_1$-$C_4$ alkyl group;
a group —OR in which R represents a hydrogen atom, a linear or branched $C_1$-$C_4$ alkyl radical; and preferably a hydroxyl group;
a group —NHCOR' or —NHSCO$_2$R' in which R' represents a hydrogen atom, a linear or branched $C_1$-$C_8$ alkyl radical, or a phenyl group optionally substituted with at least one $C_1$-$C_4$ alkyl group;
at least one of the radicals $R^1$, $R^3$ and $R^5$ representing a hydrogen atom;
two groups chosen from $R^1$, $R^2$, $R^3$, $R^4$ and $R^5$ and borne by adjacent carbon atoms may form, together with the said carbon atoms, a ring or heterocycle, optionally substituted with one or more $C_1$-$C_4$ alkyl groups, optionally interrupted with one or more groups chosen from an oxygen atom, a carbonyl group, a group —NR"— in which R" represents a hydrogen atom or a $C_1$-$C_4$ alkyl or ($C_1$-$C_4$)alkylcarbonyl radical;
formula (B1) containing only one group —NHCO— and/or at least one group —NHSO$_2$—, these groups being optionally engaged in a heterocycle.

According to one more preferred variant of the invention, the compounds of formula (B1) are ortho and/or para-amidophenol or ortho and/or para-sulfonamidophenol type i.e. particularly compounds of formula (B1) in which:

for para-amidophenol or para-sulfonamidophenol type:
$R^3$ represents a group —NHCOR' or —NHSO$_2$R' in which R' represents a hydrogen atom, a linear or branched $C_1$-$C_6$ alkyl radical, and
$R^1$, $R^2$, $R^4$ and $R^5$ are as defined herein before, and more particularly $R^1$, $R^2$, $R^4$ and $R^5$ represent a hydrogen atom or a ($C_1$-$C_4$)alkoxy group; or R' and $R^2$ or R' and $R^4$ form together a 5 to 6 members heterocycle group such as 2-pyrrolidinone, 2-pyperazinone, 2-morpolinone or 2-piperidinone;
for ortho-amidophenol or ortho-sulfonamidophenol type:
for ortho-amidophenol or ortho-sulfonamidophenol type:
$R^1$ represents a group —NHCOR' or —NHSO$_2$R' in which R' represents a hydrogen atom, a linear or branched $C_1$-$C_6$ alkyl radical, and
$R^2$, $R^3$, $R^4$ and $R^5$ are as defined herein before, and more particularly $R^2$, $R^3$, $R^4$ and $R^5$ represent a hydrogen atom or a ($C_1$-$C_4$)alkyl group; or R' and $R^2$ form together a 5 to 6 members heterocycle group such as 2-pyrrolidinone, 2-pyperazinone, 2-morpolinone or 2-piperidinone; for ortho-amidophenol or ortho-sulfonamidophenol type:

According to another preferred variant of the invention, the compounds of formula (B1) are meta-amidophenol or meta-sulfonamidophenol type i.e. particularly compounds of formula (B1) in which:
$R^2$ represents a group —NHCOR' or —NHSO$_2$R' in which R' represents a hydrogen atom, a linear or branched $C_1$-$C_6$ alkyl radical, or a phenyl group optionally substituted with at least one $C_1$-$C_4$ alkyl group; and
$R^1$, $R^3$, $R^4$ and $R^5$ are as defined herein before, and more particularly $R^1$, $R^3$, $R^4$ and $R^5$ represent a hydrogen atom or a halogen group; or R' and $R^3$ or R' and $R^1$ form together a 5 to 6 members heterocycle group such as 2-pyrrolidinone, 2-pyperazinone, 2-morpolinone or 2-piperidinone.

Preferably, the coupler(s) d) are chosen from the following compounds, and also salts thereof, optical or geometrical isomers and tautomers thereof, and hydrates thereof:

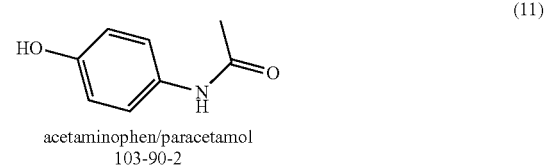

acetaminophen/paracetamol
103-90-2

(11)

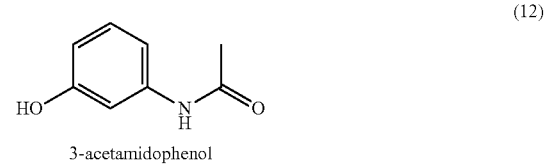

3-acetamidophenol
621-42-1

(12)

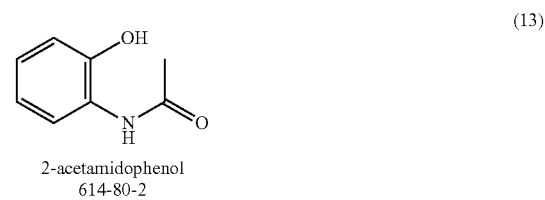

2-acetamidophenol
614-80-2

(13)

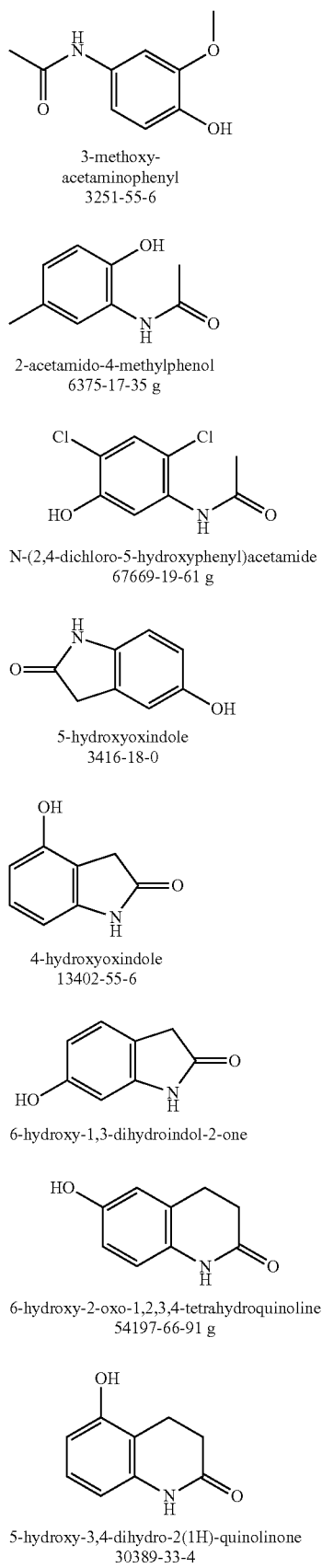
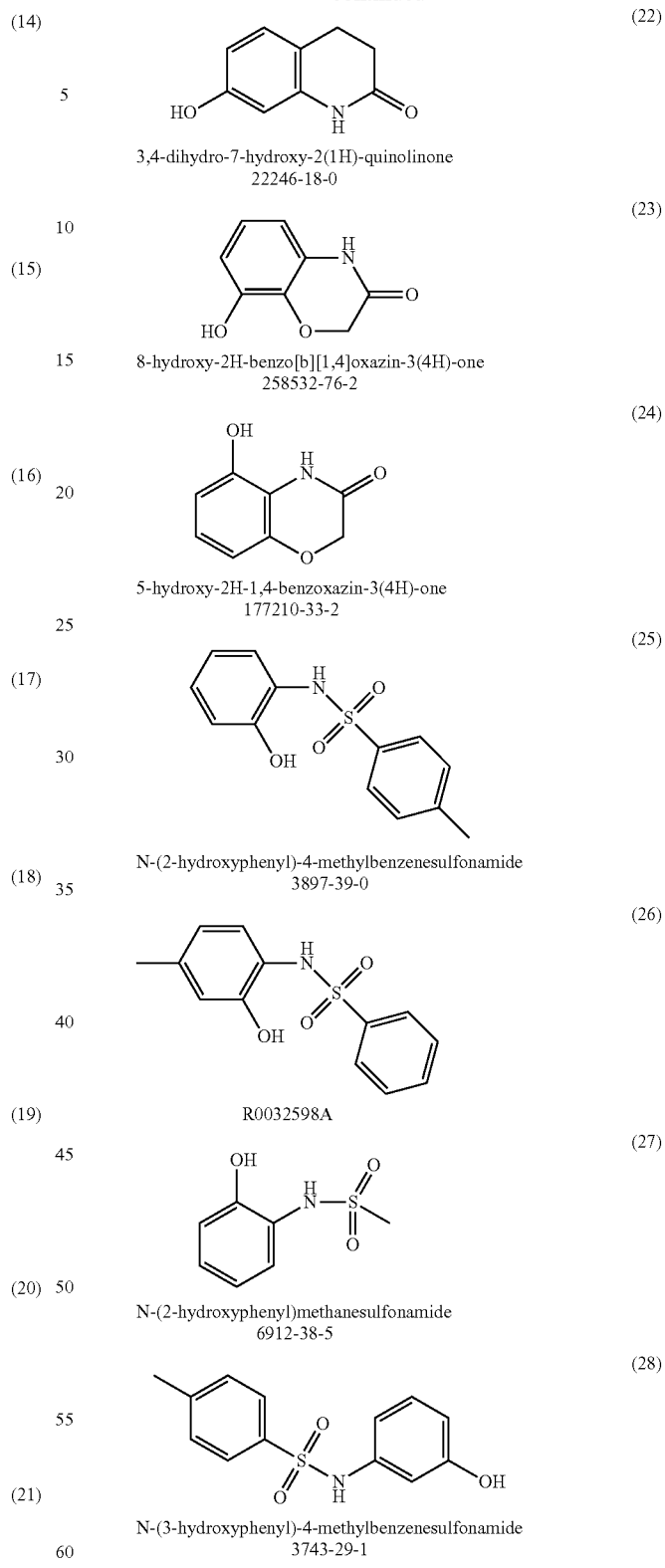
Preferably compounds of formula (B1) are para-amidophenol or para-sulfonamidophenol, particularly para-amidophenol, especially selected from compounds (II), (14), (17) and (20), or otho-amidophenol or ortho-sulfonamidophenol selected from compounds (13), (15), (24), (25), (26) and (27)

and also salts thereof, optical or geometrical isomers and tautomers thereof, and hydrates thereof.

According another preferred embodiment, compounds of formula (B1) are meta-amidophenol or meta-sulfonamidophenol, particularly meta-amidophenol, especially selected from compounds (12), (16), (18), (19), (21), (22), (23) and (28) and also salts thereof, optical or geometrical isomers and tautomers thereof, and hydrates thereof.

More preferably, the phenol-based coupler(s) of formula (B1) are chosen from the following compounds, and also salts thereof, optical or geometrical isomers and tautomers thereof, and hydrates thereof:

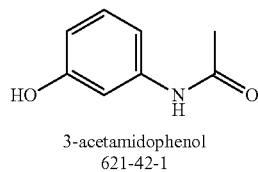

(12)

3-acetamidophenol
621-42-1

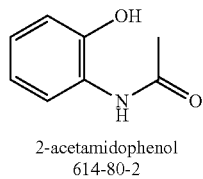

(13)

2-acetamidophenol
614-80-2

According to one particular embodiment of the invention, the coupler(s) d) included in the composition are chosen from iii) couplers of acylaminophenol type.

In particular, the coupler(s) d) are chosen from those of formula (B2) and also salts thereof, optical or geometrical isomers and tautomers thereof, and hydrates thereof;

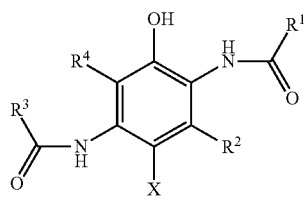

(B2)

in which formula (B2):
  $R^1$, $R^2$, $R^3$ and $R^4$, which may be identical or different, represent a linear or branched, saturated or unsaturated $C_1$-$C_{10}$ hydrocarbon-based chain, one or more of the carbon atoms of which may be replaced with an oxygen, nitrogen or sulfur atom or with a group $S(O)_2$ or with a group NR with R denoting a hydrogen atom or a $C_1$-$C_4$ alkyl radical, one or more of the carbon atoms of which chain may be substituted with one or more halogen atoms, the hydrocarbon-based chain, when it comprises from 4 to 10 carbon atoms, possibly forming one or more 3- to 8-membered rings;
  $R^2$ may represent a hydrogen atom;
  $R^4$ may represent a group —OR or —$NR_2$ in which R, which may be identical or different, represent a hydrogen atom or a $C_1$-$C_4$ alkyl radical;
  $R^3$ and $R^4$ may form, together with the carbon atoms to which each is attached, a 6- to 8-membered heterocycle comprising one or more oxygen or nitrogen heteroatoms, optionally substituted with one or more $C_1$-$C_4$ alkyl groups, and/or optionally interrupted with a carbonyl group;
  X represents a hydrogen atom, a halogen atom, a $C_1$-$C_4$ alkoxy radical or a phenoxy radical, which is optionally substituted.

According to one variant, the coupler(s) of acylaminophenol type are chosen from those of formula (B2) in which:
  $R^1$, $R^2$, $R^3$ and $R^4$, which may be identical or different, represent a linear or branched $C_1$-$C_{10}$ alkyl chain, one or more of the carbon atoms of which may be replaced with an oxygen, nitrogen or sulfur atom or with a group $SO_2$, or with a group NR with R denoting a hydrogen atom or a $C_1$-$C_4$ alkyl radical, one or more of the carbon atoms of which chain may be substituted with one or more halogen atoms;
  $R^2$ may represent a hydrogen atom;
  $R^4$ may represent a group —OR or —$NR_2$ in which R, which may be identical or different, represent a hydrogen atom or a $C_1$-$C_4$ alkyl radical;
  $R^3$ and $R^4$ may form, together with the carbon atoms to which each is attached, a 6- to 7-membered heterocycle comprising one or more oxygen or nitrogen heteroatoms, optionally substituted with one or more methyl groups, and/or optionally interrupted with a carbonyl group;
  X represents a hydrogen atom, a halogen atom, a $C_1$-$C_4$ alkoxy radical or a phenoxy radical, which is optionally substituted.

In accordance with one preferred embodiment of the invention, the coupler(s) of acylaminophenol type are chosen from those of formula (B2) in which:
  $R^1$, $R^3$ and $R^4$, which may be identical or different, represent a $C_1$-$C_4$ alkyl radical;
  $R^2$ represents a hydrogen atom;
  $R^4$ may represent a group —NHR in which R represents a $C_1$-$C_4$ alkyl radical;
  $R^3$ and $R^4$ may form, together with the carbon atoms to which each is attached, a 6- or 7-membered heterocycle, optionally substituted with one or more $C_1$-$C_4$ alkyl groups, and/or optionally interrupted with a carbonyl group;

In particular, the coupler(s) d) are chosen from those of the following formulae:

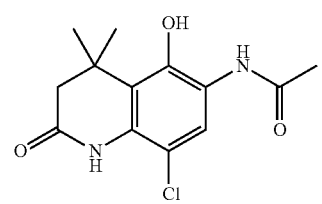

(29)

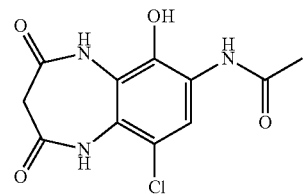

(30)

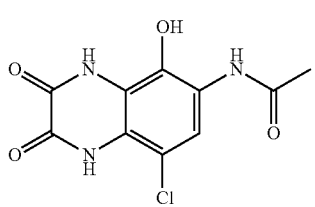 [SMILES: CC(=O)Nc1cc(Cl)c2[nH]c(=O)c(=O)[nH]c2c1O]

(30bis)

and also salts thereof, optical and geometrical isomers and tautomers thereof, and hydrates thereof.

According to one particular embodiment of the invention, the coupler(s) d) included in the composition are chosen from iv) quinoline-based couplers.

The term "quinoline couplers" means couplers bearing a quinoline or isoquinoline unit. Among the quinoline couplers, mention may be made of those of formula (B'1) or (B'2) and also salts thereof, optical or geometrical isomers and tautomers thereof, and hydrates thereof;

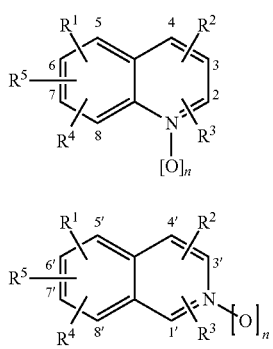

(B'1)

(B'2)

in which formulae (B'1) and (B'2):
$R^1$ represents a methyl group or an amino group;
$R^2$, $R^3$, $R^4$ and $R^5$, which may be identical or different, represent an atom or a group chosen from:
i) hydrogen;
ii) halogen such as chlorine;
iii) hydroxyl;
iv) $NR^aR^b$ with $R^a$ and $R^b$, which may be identical or different, representing a hydrogen atom or a $(C_1-C_8)$ alkyl group optionally substituted with a hydroxyl group or a $(di)(C_1-C_8)(alkyl)$amino group;
or alternatively $R^a$ and $R^b$, with the nitrogen atom, together form a saturated or partially unsaturated 3- to 10-membered mono- or polycyclic heterocycle containing from 1 to 5 heteroatoms chosen from oxygen, nitrogen, sulfur, sulfoxide S(O) and sulfone $S(O)_2$, the heterocycle possibly being substituted with a group $(C_1-C_4)$alkyl or an oxo group; in particular, the heterocycle is chosen from morpholino, piperidino and piperazino;
v) $(C_1-C_8)$alkyl optionally substituted with one or more atoms or groups chosen from halogen such as fluorine, hydroxyl and amino $NR^aR^b$ as defined previously;
vi) $(C_1-C_8)$alkoxy;
vii) $(C_1-C_8)$alkyl-$S(O)_p$— with p=0, 1 or 2; and
viii) aryloxy such as phenoxy;
or alternatively two contiguous radicals $R^2$ and $R^3$ form, together with the carbon atoms to which each is attached, a (hetero)cycle or a (hetero)aryl optionally substituted with a) a halogen atom, b) a hydroxyl or c) an amino group $NR^aR^b$ as defined previously, d) $(C_1-C_8)$ alkyl optionally substituted with one or more groups chosen from halogen such as fluorine, hydroxyl and amino $NR^aR^b$ as defined previously, e) $(C_1-C_8)$alkoxy, f) $(C_1-C_8)$alkyl-$S(O)_p$— with p=0, 1 or 2;
preferentially $R^2$ and $R^3$ together form a benzo group and, more particularly in formula (B1), the groups $R^2$ and $R^3$ are in position 2 and 3 and together form a benzo group;
n is 0 or 1 and preferentially n is 0.

According to one particular embodiment of the invention, the quinoline coupler(s) of formula (B'1) or (B'2) are such that $R^2$, $R^3$, $R^4$ and $R^5$, which may be identical or different, represent:
a hydrogen atom;
a halogen atom such as chlorine;
or a group chosen from:
hydroxyl;
$(C_1-C_6)$alkyl such as methyl, ethyl or propyl;
(poly)haloalkyl such as trifluoromethyl;
(di) $(C_1-C_6)$(alkyl)amino;
(di)$(C_1-C_6)$(alkyl)amino$(C_1-C_6)$(alkyl)amino; and
$NR^aR^b$ in which $R^a$ and $R^b$, with the nitrogen atom together form a saturated monocyclic 5- to 7-membered heterocycle comprising from 1 to 3 heteroatoms chosen from oxygen and nitrogen, the heterocycle possibly being substituted with a group $(C_1-C_4)$alkyl; in particular, the heterocycle is chosen from morpholino, piperidino and piperazino, and more preferably the heterocycle is piperidino,
or alternatively two contiguous radicals $R^2$ and $R^3$ together form a benzo group; preferentially, the groups $R^2$ and $R^3$ are in position 2 and 3 and together form a benzo group.

According to one preferred embodiment of the invention, the quinoline coupler(s) are chosen from those of formula (B'1).

According to one particular mode of the invention, $R^1$ represents a hydroxyl group.

More particularly, the quinoline coupler(s) of formula (B'1) are such that $R^1$ represents a hydroxyl group in position 8 and $R^2$, $R^3$, $R^4$ and $R^5$, which may be identical or different, represent a hydrogen or halogen atom, preferably in position 6 or 7; a group $(C_1-C_6)$alkyl preferably in position 2, 4 or 7; a group $(C_1-C_6)$alkoxy preferably in position 2, 4 or 6; a group $(C_1-C_6)$(alkyl)amino preferably in position 2; a piperidino group preferably in position 2; a hydroxyl group preferably in position 2; a trihalo$(C_1-C_4)$alkyl group such as trifluoromethyl, preferably in position 2 and/or $R^2$ and $R^3$ are in position 2 and 3 and together form a benzo group.

According to another variant, $R^1$ represents a hydroxyl group in position 7 and $R^2$, $R^3$, $R^4$ and $R^5$, which may be identical or different, represent a hydrogen atom; a halogen atom preferably in position 4; a hydroxyl group preferably in position 2; or a trihalo$(C_1-C_4)$alkyl group such as trifluoromethyl, preferably in position 4.

According to another variant, $R^1$ represents a hydroxyl group in position 6 and $R^2$, $R^3$, $R^4$ and $R^5$, which may be identical or different, represent a hydrogen atom; a halogen atom preferably in position 2, 4 and 8; an amino group preferably in position 2; a $(C_1-C_6)$alkyl group preferably in position 2 or 4; or a hydroxyl group preferably in position 4 or 5.

According to another variant, $R^1$ represents a hydroxyl group in position 5 and $R^2$, $R^3$, $R^4$ and $R^5$ represent a hydrogen atom and/or $R^2$ and $R^3$ are in position 2 and 3 and together form a benzo group.

According to another advantageous mode of the invention, $R^1$ represents an amino group.

More particularly, quinoline coupler(s) of formula (B1) are such that $R^1$ represents an amino group in position 8 and $R^2$, $R^3$, $R^4$ and $R^5$, which may be identical or different, represent a hydrogen atom; a ($C_1$-$C_6$)alkyl group preferably in position 2, 4, 6 or 7; a group ($C_1$-$C_6$)alkoxy preferably in position 4 or 6; or a hydroxyl group preferably in position 4.

According to another variant, $R^1$ represents an amino group in position 7 and $R^2$, $R^3$, $R^4$ and $R^5$, which may be identical or different, represent a hydrogen atom; or a group ($C_1$-$C_6$)alkyl group preferably in position 4.

According to another variant, $R^1$ represents an amino group in position 6 and $R^2$, $R^3$, $R^4$ and $R^5$, which may be identical or different, represent a hydrogen atom; a hydroxyl group preferably in position 4; a trihalo($C_1$-$C_4$)alkyl such as trifluoromethyl, preferably in position 2; a group ($C_1$-$C_6$)alkyl preferably in position 2; an amino group in position 4; a group ($C_1$-$C_6$)alkoxy preferably in position 8 or a group (di)($C_1$-$C_6$)(alkyl)amino($C_1$-$C_6$)(alkyl)amino preferably in position 4.

According to another variant, $R^1$ represents an amino group in position 5 and $R^2$, $R^3$, $R^4$ and $R^5$ represent a hydrogen atom or a group ($C_1$-$C_6$)alkyl preferably in position 2, 6 or 7 or a group (di)($C_1$-$C_6$)(alkyl)amino preferably in position 6.

According to another embodiment of the invention, the quinoline coupler(s) are chosen from those of formula (B'2). According to this particular mode, $R^1$ advantageously represents a hydroxyl group in position 5', 6', 7' and 8' and, preferentially, $R^2$, $R^3$, $R^4$ and $R^5$, which may be identical or different, represent a hydrogen atom or a hydroxyl group, in particular in position 1'. According to another variant, $R^1$ advantageously represents an amino group in position 5', 6', 7' and 8' and, preferentially, $R^2$, $R^3$, $R^4$ and $R^5$ represent a hydrogen atom.

As examples of couplers d) according to the invention, mention may be made of compounds (31) to (99) below:

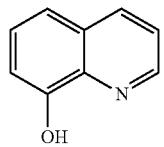

(31)

8-hydroxyquinoline
148-24-3

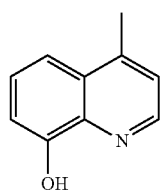

(32)

4-methyl-8-hydroxyquinoline:
3846-73-9

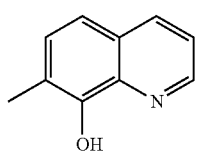

(33)

7-methyl-8-hydroxyquinoline:
5541-68-4

(34)

2-methyl-8-hydroxyquinoline:
826-81-3

(35)

2-amino-8-hydroxyquinoline:
70125-16-5

(36)

2,8-quinolinediol:
15450-76-7

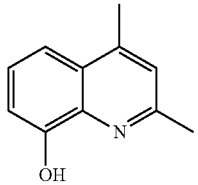

(37)

2,6-dimethyl-8-hydroxyquinoline:
115310-98-0

(38)

2-(methylamino)-8-quinolinol:
70125-17-6

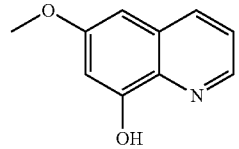

(39)

6-methoxy-8-quinolinol:
477601-28-8

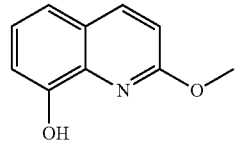

(40)

2-methoxy-8-quinolinol:
74668-72-7

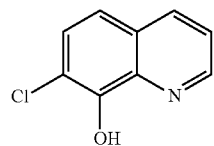

7-chloro-8-hydroxyquinoline:
876-86-8

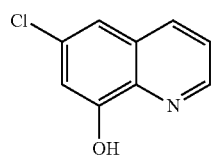

6-chloro-8-hydroxyquinoline:
18119-24-9

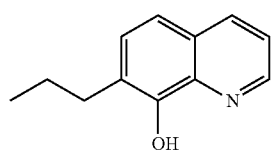

7-N-propyl-8-hydroxyquinoline:
58327-60-9

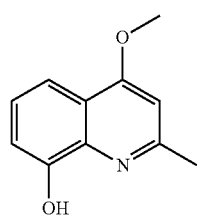

4-methoxy-2-methyl-8-hydroxyquinoline:
167834-50-6

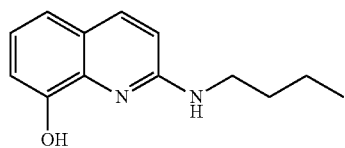

2-(n-butylamino)-8-hydroxyquinoline:
70125-20-1

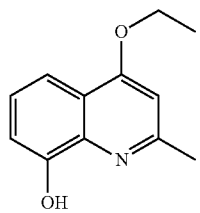

4-ethoxy-2-methyl-
8-hydroxyquinoline:
167834-51-7

(41)

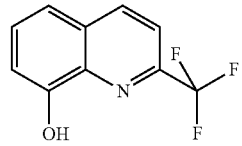

2-trifluoromethyl-
8-hydroxyquinoline:
41192-80-7

(42)

2-(1-piperidinyl)-8-
hydroxyquinoline:
31570-94-2

(43)

7-hydroxyquinoline
580-20-1

(44)

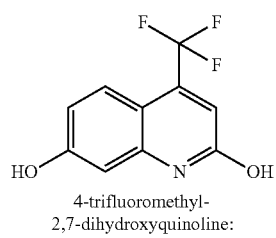

4-trifluoromethyl-
2,7-dihydroxyquinoline:
73496-29-4

(45)

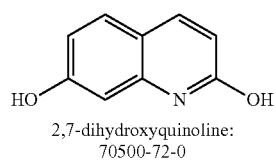

2,7-dihydroxyquinoline:
70500-72-0

(46)

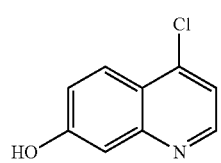

4-chloro-7-
hydroxyquinoline:
181950-57-2

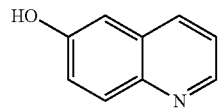

6-hydroxyquinoline
580-16-5

(47)

(48)

(49)

(50)

(51)

(52)

(53)

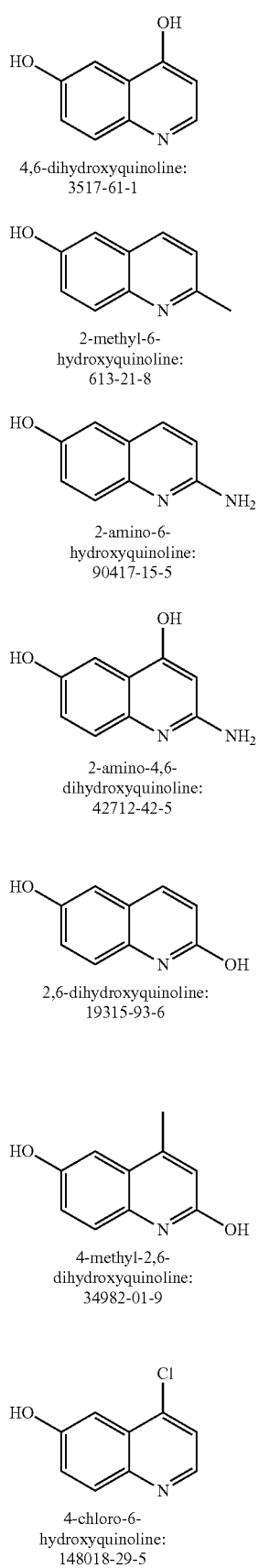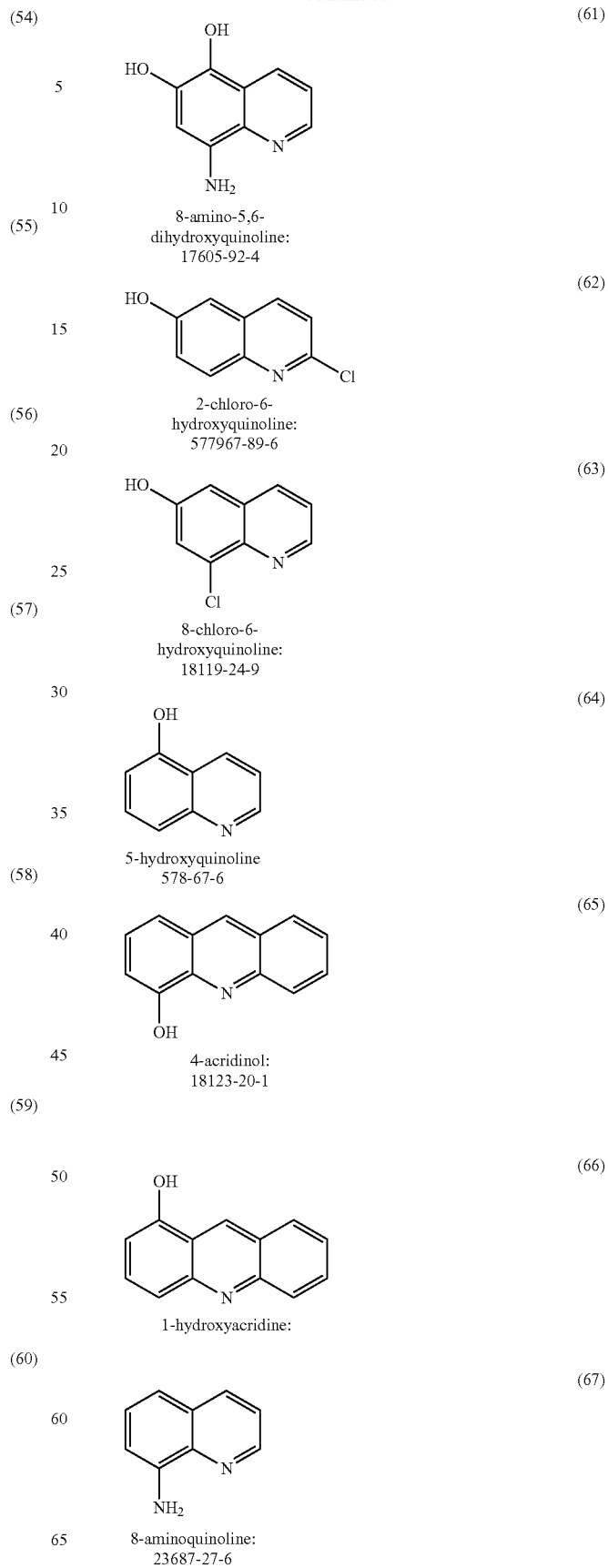

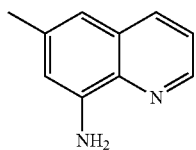
(68) 6-methyl-8-aminoquinoline
(69) 2-methyl-8-aminoquinoline: 18978-78-4
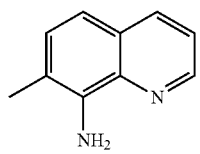
(70) 7-methyl-8-aminoquinoline: 5470-82-6
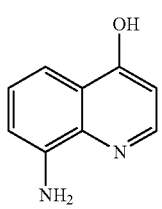
(71) 8-amino-4-hydroxyquinoline: 53867-95-1
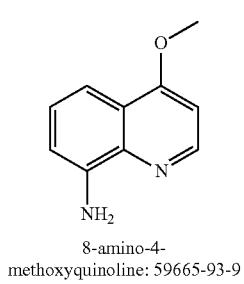
(72) 8-amino-4-methoxyquinoline: 59665-93-9
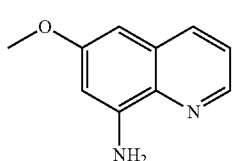
(73) 8-amino-6-methoxyquinoline: 90-52-8
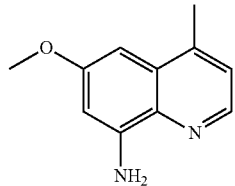
(74) 8-amino-6-methoxy-4-methylquinoline 57514-21-3
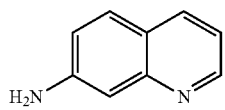
(75) 7-aminoquinoline: 580-19-8
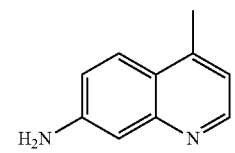
(76) 4-methyl-7-aminoquinoline: 114058-79-6
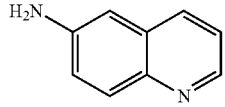
(77) 6-aminoquinoline: 580-15-4
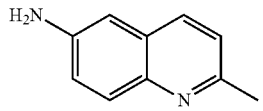
(78) 2-methyl-6-aminoquinoline: 65079-19-8
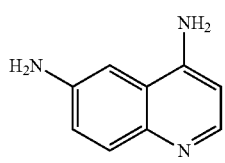
(79) 4,6-diaminoquinoline: 40107-09-3
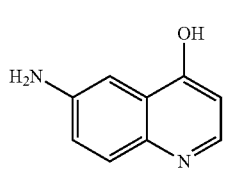
(80) 4-hydroxy-6-aminoquinoline:

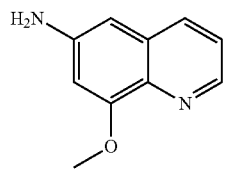

(81)

8-methoxy-6-aminoquinoline: 75959-08-9

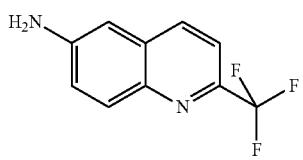

(82)

2-trifluoromethyl-6-aminoquinoline: 952182-53-5

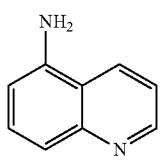

(83)

5-aminoquinoline: 611-34-7

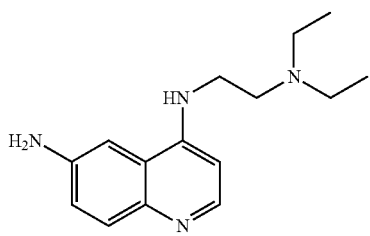

(84)

6-amino-4((2-(diethylamino)ethylamino)quinoline (diphosphate salt, 2PO$_4^{3-}$) 78703-87-4

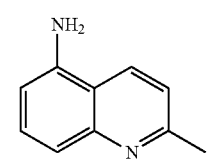

(85)

2-methyl-5-aminoquinoline: 54408-50-3

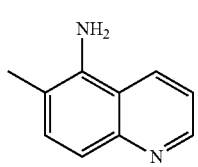

(86)

6-methyl-5-aminoquinoline: 50358-35-5

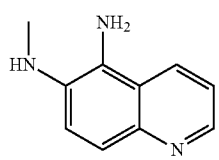

(87)

6-methyaminol-5-aminoquinoline: 14204-98-9

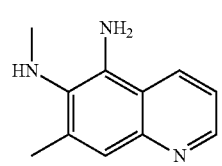

(88)

5-amino-6-methylaminol-7-methylquinoline: 83407-42-5

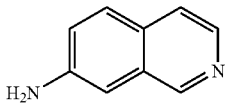

(89)

7-aminoisoquinoline: 23707-37-1

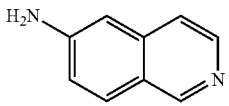

(90)

6-aminoisoquinoline: 23687-26-5

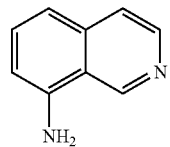

(91)

8-aminoisoquinoline: 23687-27-6

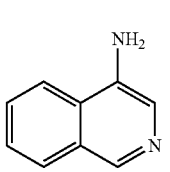

(92)

4-aminoisoquinoline: 23687-25-4

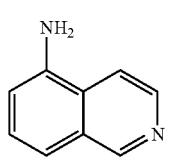

(93)

5-aminoisoquinoline: 1125-60-6

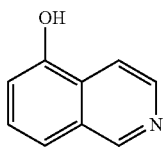

5-hydroxyisoquinoline:
2439-04-5

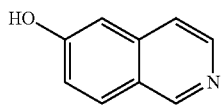

6-hydroxyisoquinoline:
7651-82-3

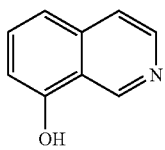

8-hydroxyisoquinoline:
3482-14-2

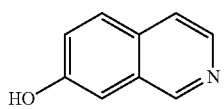

7-hydroxyisoquinoline:
7651-83-4

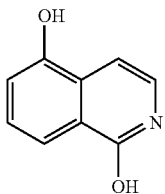

1,5-isoquinolinediol: 5154-02-9

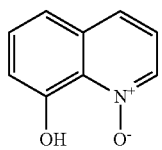

8-hydroxyquinoline N-oxide:
1127-45-3

The coupler(s) d) as defined previously each advantageously represent from 0.0001% to 10% by weight relative to the total weight of the composition, and preferably from 0.005% to 5% by weight relative to the total weight of the composition of the invention.

Additional Couplers

The composition of the invention may comprise one or more couplers other than the couplers d) as defined previously.

Among these additional couplers, mention may be made especially of meta-phenylenediamines, meta-aminophenols, meta-diphenols, naphthalene-based couplers other than 2-hydroxynaphthalene couplers, and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(n-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzo-morpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

The additional coupler(s) each advantageously represent from 0.0001% to 10% by weight relative to the total weight of the composition, and preferably from 0.005% to 5% by weight relative to the total weight of the composition of the invention.

In general, the addition salts of the oxidation bases and couplers that may be used in the context of the invention are especially selected from the addition salts with an acid such as the hydrochlorides, hydrobromides, sulfates, citrates, succinates, tartrates, lactates, tosylates, benzenesulfonates, phosphates and acetates.

Additional Dyes

The composition according to the invention may also comprise one or more direct dyes. The latter dyes are more particularly chosen from ionic or nonionic species, preferably cationic or nonionic species. These direct dyes may be synthetic or of natural origin.

Examples of suitable direct dyes that may be mentioned include azo dyes; methine dyes; carbonyl dyes; azine dyes; nitro (hetero)aryl dyes; tri(hetero)arylmethane dyes; porphyrin dyes; phthalocyanine dyes, and natural direct dyes, alone or as mixtures.

More particularly, the azo dyes comprise an —N═N— function in which the two nitrogen atoms are not simultaneously engaged in a ring. However, it is not excluded for one of the two nitrogen atoms of the sequence —N═N— to be engaged in a ring.

The dyes of the methine family are more particularly compounds comprising at least one sequence selected from >C═C< and —N═C< in which the two atoms are not simultaneously engaged in a ring. However, it is pointed out that one of the nitrogen or carbon atoms of the sequences may be engaged in a ring. More particularly, the dyes of this family are derived from compounds of the type such as methines, azomethines, mono- and diarylmethanes, indoamines (or diphenylamines), indophenols, indoanilines, carbocyanins, azacarbocyanins and isomers thereof, diazacarbocyanins and isomers thereof, tetraazacarbocyanins and hemicyanins.

As regards the dyes of the carbonyl family, examples that may be mentioned include dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin.

As regards the dyes of the cyclic azine family, mention may be made especially of azine, xanthene, thioxanthene, fluorindine, acridine, (di)oxazine, (di)thiazine and pyronin.

The nitro(hetero)aromatic dyes are more particularly nitrobenzene or nitropyridine direct dyes.

As regards the dyes of porphyrin or phthalocyanin type, it is possible to use cationic or non-cationic compounds, optionally comprising one or more metals or metal ions, for instance alkali metals, alkaline-earth metals, zinc and silicon.

Examples of particularly suitable direct dyes that may be mentioned include nitrobenzene dyes; azo direct dyes; azomethine direct dyes; methine direct dyes; azacarbocyanin direct dyes, for instance tetraazacarbocyanins (tetraazapentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanine direct dyes, porphyrin direct dyes and natural direct dyes, alone or as mixtures.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the direct dye(s) more particularly represent from 0.0001% to 10% by weight and preferably from 0.005% to 5% by weight of the total weight of the composition.

e) The Basifying Agents:

The composition of the invention also comprises e) one or more basifying agents. The basifying agent(s) may be mineral or organic or hybrid.

The mineral basifying agent(s) are preferably chosen from aqueous ammonia, alkali metal carbonates or bicarbonates such as sodium or potassium carbonates and sodium or potassium bicarbonates, sodium hydroxide or potassium hydroxide, or mixtures thereof.

The organic basifying agent(s) are preferably chosen from organic amines with a $pK_b$ at 25° C. of less than 12, preferably less than 10 and even more advantageously less than 6. It should be noted that it is the $pK_b$ corresponding to the function of highest basicity. In addition, the organic amines do not comprise any alkyl or alkenyl fatty chains comprising more than ten carbon atoms.

The organic basifying agent(s) are chosen, for example, from alkanolamines, oxyethylenated and/or oxypropylenated ethylenediamines, amino acids and the compounds of formula (I) below:

$$R_x \diagdown N - W - N \diagup R_z \atop R_y \diagup \qquad \diagdown R_t \quad (I)$$

in which formula (I) W is a $C_1$-$C_6$ divalent alkylene radical optionally substituted with one or more hydroxyl groups or a $C_1$-$C_6$ alkyl radical, and/or optionally interrupted with one or more heteroatoms such as O, or $NR_u$; $R_x$, $R_y$, $R_z$, $R_t$ and $R_u$, which may be identical or different, represent a hydrogen atom or a $C_1$-$C_6$ alkyl or $C_1$-$C_6$ hydroxyalkyl or $C_1$-$C_6$ aminoalkyl radical.

Examples of amines of formula (I) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (II) below:

$$R-CH_2-CH\diagup^{NH_2}_{CO_2H} \quad (II)$$

in which formula (II) R represents a group chosen from:

[imidazole ring structure];

—$(CH_2)_3NH_2$;
—$(CH_2)_2NH_2$; —$(CH_2)_2NHCONH_2$; and

—$(CH_2)_2NH-\underset{\underset{NH}{\|}}{C}-NH_2$

The compounds corresponding to formula (II) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and baleine.

The organic amine may also be chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the basifying agent(s) present in the composition of the invention are chosen from alkanolamines, amino acids in neutral or ionic form, in particular basic amino acids, and preferably corresponding to those of formula (II). Even more preferentially, the basifying agent(s) are chosen from monoethanolamine (MEA) and basic amino acids, in neutral or ionic form.

Advantageously, the composition according to the invention has a content of basifying agent(s) ranging from 0.01% to 30% by weight and preferably from 0.1% to 20% by weight relative to the weight of the composition.

According to a first particular embodiment, the composition does not contain any aqueous ammonia or salt thereof, or the process according to the invention does not use any aqueous ammonia or salt thereof as basifying agent.

According to another particular mode, if, however, it were used in the composition or the process, its content would advantageously not exceed 0.03% by weight (expressed as $NH_3$) and preferably would not exceed 0.01% by weight relative to the weight of the composition. Preferably, if the composition comprises aqueous ammonia, or a salt thereof, then the amount of basifying agent(s) other than aqueous ammonia is greater than that of the aqueous ammonia (expressed as $NH_3$).

f) Chemical Oxidizing Agent

The composition of the invention may also comprise f) one or more chemical oxidizing agents. The term "chemical oxidizing agent" means an oxidizing agent other than atmospheric oxygen. Preferentially, the composition of the invention contains one or more chemical oxidizing agents.

More particularly, the chemical oxidizing agent(s) are chosen from hydrogen peroxide, urea peroxide, alkali metal bromates, peroxygenated salts, for instance persulfates, perborates, peracids and precursors thereof and percarbonates of alkali metals or alkaline-earth metals.

This oxidizing agent is advantageously formed from hydrogen peroxide especially in aqueous solution (aqueous hydrogen peroxide solution), the concentration of which may range more particularly from 0.1% to 50% by weight, even more preferentially from 0.5% to 20% by weight and better still from 1% to 15% by weight relative to the weight of the composition.

Preferably, the composition of the invention does not contain any peroxygenated salts.

Solvent

The composition according to the invention may also comprise one or more organic solvents.

Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The solvent(s), if they are present, represent a content usually ranging from 1% to 40% by weight and preferably from 5% to 30% by weight relative to the weight of the composition.

Other Additives

The composition according to the invention may also contain various adjuvants conventionally used in hair dye compositions, such as anionic, cationic, nonionic, amphoteric or zwitterionic polymers or mixtures thereof; mineral thickeners, and in particular fillers such as clays, talc; organic thickeners with, in particular, anionic, cationic, nonionic and amphoteric polymeric associative thickeners; antioxidants; penetrants; sequestrants; fragrances; dispersants; film-forming agents; ceramides; preserving agents; opacifiers.

The above adjuvants are generally present in an amount for each of them of between 0.01% and 20% by weight relative to the weight of composition.

The composition may especially comprise one or more mineral thickeners chosen from organophilic clays and fumed silicas, or mixtures thereof.

The organophilic clay may be chosen from montmorillonite, bentonite, hectorite, attapulgite and sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulfates, alkylarylsulfonates and amine oxides, and mixtures thereof.

Organophilic clays that may be mentioned include quaternium-18 bentonites such as those sold under the names Bentone 3, Bentone 38 and Bentone 38V by the company Rheox, Tixogel VP by the company United Catalyst, Claytone 34, Claytone 40 and Claytone XL by the company Southern Clay; stearalkonium bentonites such as those sold under the names Bentone 27 by the company Rheox, Tixogel LG by the company United Catalyst and Claytone AF and Claytone APA by the company Southern Clay; quaternium-18/benzalkonium bentonites such as those sold under the names Claytone HT and Claytone PS by the company Southern Clay.

The fumed silicas may be obtained by high-temperature hydrolysis of a volatile silicon compound in an oxhydric flame, producing a finely divided silica. This process makes it possible especially to obtain hydrophilic silicas having a large number of silanol groups at their surface. Such hydrophilic silicas are sold, for example, under the names Aerosil 130®, Aerosil 200®, Aerosil 255®, Aerosil 300® and Aerosil 380® by the company Degussa, and Cab-O-Sil H55®, Cab-O-Sil EH-5®, Cab-O-Sil LM-130®, Cab-O-Sil MS-55® and Cab-O-Sil M-5® by the company Cabot.

It is possible to chemically modify the surface of the silica via chemical reaction in order to reduce the number of silanol groups. It is especially possible to substitute silanol groups with hydrophobic groups: a hydrophobic silica is then obtained.

The hydrophobic groups may be:
trimethylsiloxyl groups, which are obtained especially by treating fumed silica in the presence of hexamethyldisilazane. Silicas thus treated are known as "silica silylate" according to the CTFA (6th Edition, 1995). They are sold, for example, under the references Aerosil R812® by the company Degussa and Cab-O-Sil TS-530® by the company Cabot.
dimethylsilyloxyl or polydimethylsiloxane groups, which are especially obtained by treating fumed silica in the presence of polydimethylsiloxane or dimethyldichlorosilane. Silicas thus treated are known as "silica dimethyl silylate" according to the CTFA (6th Edition, 1995). They are sold, for example, under the references Aerosil R972® and Aerosil R974® by the company Degussa, and Cab-O-Sil TS-610® and Cab-O-Sil TS-720® by the company Cabot.

The fumed silica preferably has a particle size that may be nanometric to micrometric, for example ranging from about 5 to 200 nm.

Preferably, the composition comprises a hectorite, an organomodified bentonite or an optionally modified fumed silica.

When it is present, the mineral thickener represents from 1% to 30% by weight relative to the weight of the composition.

The composition may also comprise one or more organic thickeners.

These thickeners may be chosen from fatty acid amides (coconut monoethanolamide or diethanolamide, oxyethylenated carboxylic acid monoethanolamide alkyl ether), polymeric thickeners such as cellulose-based thickeners (hydroxyethylcellulose, hydroxypropylcellulose or carboxymethylcellulose), guar gum and derivatives thereof (hydroxypropyl guar), gums of microbial origin (xanthan gum, scleroglucan gum), acrylic acid or acrylamidopropanesulfonic acid crosslinked homopolymers and associative polymers (polymers comprising hydrophilic regions and fatty-chain hydrophobic regions (alkyl or alkenyl containing at least 10 carbon atoms) that are capable, in an aqueous medium, of reversibly combining with each other or with other molecules).

According to one particular embodiment, the organic thickener is chosen from cellulose-based thickeners (hydroxyethylcellulose, hydroxypropylcellulose or carboxymethylcellulose), guar gum and derivatives thereof (hydroxypropyl guar), gums of microbial origin (xanthan gum, scleroglucan gum) and acrylic acid or acrylamidopropanesulfonic acid crosslinked homopolymers, and preferably from cellulose-based thickeners in particular with hydroxyethylcellulose.

The content of organic thickener(s), if they are present, usually ranges from 0.01% to 20% by weight and preferably from 0.1% to 5% by weight relative to the weight of the composition.

The composition of the invention may be in various forms, for instance a solution, an emulsion (milk or cream) or a gel.

Processes of the Invention:

The composition according to the invention comprising ingredients a) to f) as defined previously is applied to wet or dry keratin fibres. It is left in place on the fibres for a time generally of from 1 minute to 1 hour and preferably from 5 minutes to 30 minutes.

The temperature during the dyeing process is conventionally between room temperature (between 15 and 25° C.) and 80° C. and preferably between room temperature and 60° C.

After the treatment, the human keratin fibres are optionally rinsed with water, optionally washed with a shampoo and then rinsed with water, before being dried or left to dry.

The composition according to the invention is generally prepared by mixing at least two compositions.

In a first variant of the invention, the composition according to the invention comprising ingredients a) to f) as defined previously is derived from the mixing of two compositions:
a composition (A) comprising c) at least one oxidation base as defined previously; d) at least one coupler chosen from i) 2-hydroxynaphthalene derivatives, ii) the phenols of formula (B1), iii) the acylaminophenols as defined previously and iv) the quinoline derivatives as defined previously; e) at least one basifying agent as defined previously; and
a composition (B) comprising f) at least one chemical oxidizing agent as defined previously,
it being understood that:
at least one of the compositions (A) and (B) comprises a) at least one fatty substance as defined previously, and b) at least one surfactant as defined previously, such that the fatty substance content of the composition according to the invention resulting from the mixing of compositions (A)+(B) comprises at least 25% fatty substance.

Preferentially, at least one of the compositions (A) or (B) is aqueous.

Even more preferentially, both the compositions (A) and (B) are aqueous.

The term "aqueous composition" means a composition comprising at least 5% water. Preferably, an aqueous formulation comprises more than 10% by weight of water and even more advantageously more than 20% by weight of water.

Composition (A) is preferably aqueous.

In this variant, composition (A) comprises at least 50% of fatty substances and even more preferentially at least 50% of fatty substances that are liquid at room temperature (25° C.).

Preferably, composition (A) is a direct or inverse emulsion, and preferably a direct emulsion (O/W).

In this variant, compositions (A) and (B) are preferably mixed together in a weight ratio (A)/(B) ranging from 0.2 to 10 and better still from 0.5 to 2.

According to a second variant of the invention, the composition according to the invention comprising ingredients a) to f) as defined previously is derived from the mixing of three compositions, the three compositions being aqueous or at least one of them being anhydrous.

More particularly, for the purposes of the invention, the term "anhydrous cosmetic composition" means a cosmetic composition with a water content of less than 5% by weight, preferably less than 2% by weight and even more preferably less than 1% by weight relative to the weight of the said composition. It should be noted that the water present in the composition is more particularly "bound water", such as water of crystallization in salts, or traces of water absorbed by the starting materials used in the preparation of the compositions according to the invention.

In this second variant, it will be preferred to use two aqueous compositions (B') and (C') and an anhydrous composition (A'). In this case, the anhydrous composition (A') preferably comprises a) at least one fatty substance as defined previously and more preferentially at least one liquid fatty substance. In this case, composition (B') preferably comprises c) at least one oxidation base as defined previously and d) at least one coupler chosen from i) 2-hydroxynaphthalene derivatives, ii) the phenols of formula (B1), iii) the acylaminophenols as defined previously and iv) the quinoline derivatives as defined previously. In this case, composition (C') preferably comprises f) at least one chemical oxidizing agent as defined previously. The basifying agent(s) e) as defined previously are included in compositions (A') and/or (B') and preferably solely in composition (B'). The surfactant(s) as defined previously are included in at least one of the compositions (A') or (B') or (C'), these three compositions being such that the fatty substance content of the composition according to the invention resulting from the mixing of the three compositions (A')+(B')+(C') comprises at least 25% fatty substances.

In this variant, compositions (A'), (B') and (C') are preferably mixed together in a weight ratio [(A')+(B')]/(C') ranging from 0.2 to 10 and more particularly from 0.5 to 2 and in a weight ratio (A')/(B') ranging from 0.5 to 10 and preferably from 1 to 5.

Finally, the invention relates to a first multi-compartment device comprising a first compartment containing composition (A) as described above and at least one second compartment containing composition (B) as described above, the compositions of the compartments being intended to be mixed together before application, to give the formulation after mixing according to the invention, provided that the amount of fatty substance in this formulation represents at least 25% by weight relative to the weight of the formulation derived from the mixture of (A)+(B).

The invention also relates to a second multi-compartment device comprising a first compartment containing composition (A') as described above and a second compartment containing a composition (B') as described above, and a third compartment comprising composition (C') as described above, the compositions of the compartments being intended to be mixed together before application, to give the formulation after mixing according to the invention, provided that the amount of fatty substance in this formulation represents at least 25% by weight relative to the weight of the formulation derived from the mixture of (A')+(B')+(C').

The examples that follow serve to illustrate the invention without, however, being limiting in nature.

EXAMPLES

Example 1

With a 2-Hydroxynaphthyl-Based Coupler d)

The following compositions are prepared, in which the amounts are expressed in grams of active materials.

Composition A1:

| Ingredients | A1 |
|---|---|
| Liquid petroleum jelly (fatty substance) | 64.5 |
| 2-Octyldodecanol (fatty substance) | 11.5 |
| Distearyldimethylammonium-modified hectorite | 3 |
| Propylene carbonate | 1 |
| Oxyethylenated sorbitan monolaurate (4 OE) (surfactant) | 11 |
| Glycol distearate | 8 |
| Oxyethylenated lauryl alcohol (2 OE) (surfactant) | 1 |

Composition B1:

| Ingredients | B1 |
|---|---|
| Propylene glycol | 6.2 |
| Ethyl alcohol | 8.25 |
| Hexylene glycol (2-methyl-2,4 pentanediol) | 3 |
| Dipropylene glycol | 3 |
| Monoethanolamine (basifying agent) | 14.5 |
| Sodium metabisulfite | 0.7 |
| Vitamin C: L-ascorbic acid | 0.25 |
| Diethylenetriaminepentaacetic acid, pentasodium salt as a 40% aqueous solution | 1 |
| Hydroxyethylcellulose (Natrosol 250 HHR, Aqualon) | 3.5 |
| Oxidation base | $2 \times 10^{-2}$ mol |
| Coupler | $2 \times 10^{-2}$ mol |
| Water | qs 100 g |

Composition C1 (Chemical Oxidizing Agent):

| Ingredients | C1 |
|---|---|
| Cetylstearyl alcohol (Nafol 1618F) (fatty substance) | 8 |
| Glycerol | 0.5 |
| Liquid petroleum jelly (fatty substance) | 20 |
| Oxyethylenated cetylstearyl alcohol (33 OE) (surfactant) | 3 |
| Oxyethylenated rapeseed acid amide (4 OE) (surfactant) | 1.2 |
| Tetrasodium pyrophosphate | 0.03 |
| Diethylenetriaminepentaacetic acid, pentasodium salt as a 40% aqueous solution | 0.15 |
| Phosphoric acid | 0.1 |
| Tetramethylhexamethylenediamine/1,3-dichloro-propylene polycondensate (aqueous 40% solution) | 0.1 |
| Polydimethyldiallylammonium chloride (aqueous 40% solution) | 0.2 |
| Hydrogen peroxide as an aqueous 50% solution (chemical oxidizing agent) | 6 |
| Sodium stannate | 0.04 |
| Vitamin E | 0.1 |
| Phosphoric acid | qs pH 2.2 |
| Water | qs 100 g |

At the time of use, the following are mixed together (on a weight basis):
  10 parts of composition A1
  4 parts of composition B1
  16 parts of composition C1

The mixture obtained is then applied to hair that is 90% grey. The "mixture/lock" bath ratio is 10/1 (g/g). The leave-on time is preferentially 30 minutes at 27° C.

After this time, the locks are rinsed, and then washed with shampoo and dried

The results obtained with the composition of the invention were compared with those obtained with a prior art composition (Recital®) containing in the mixture with the oxidizing agent the same dyes at the same concentrations.

Calculation of the Colour Variation ($\Delta E_{Lab}*$)

The colour build-up ($\Delta E_{Lab}*$) was evaluated in the CIE L* a* b* system. In this L*, a*, b* system, L* represents the intensity of the colour, a* indicates the green/red colour axis and b* the blue/yellow colour axis. The lower the value of L*, the darker or more intense the colour.

The value of $\Delta E_{Lab}*$ was calculated from the values of L*a*b* according to equation (i) below:

$$\Delta E_{Lab}* = \sqrt{(L*-L_o*)^2 + (a*-a_o*)^2 + (b*-b_o*)^2} \quad (i)$$

The colour build-up ($\Delta E_{Lab}*$) was calculated on locks of untreated hair ($L_o*$, $a_o*$ and $b_o*$) and on locks of dyed hair (L*, a* and b*). The L*, a*, b* values for the untreated Natural Grey (NG) hair are as follows L*=57.93, a*=0.76, b*=14.32.

The greater the value of $\Delta E_{Lab}*$, the better the coverage of the treated fibres and thus of the roots.

Calculation of the Light-Fastness ($\Delta E_{light*}$)
  machine: Suntest XLS+(from Atlas) equipped with an infrared quartz filter and a special UV filter, xenon arc lamp (2200 W)
  principle: the locks are fixed onto card supports, one half of the lock being obscured with a card. The sample holders are placed in the machine on horizontal plates arranged under the lamp, for 18 hours.

The light-fastness is evaluated by determining the $\Delta E_{light*}$
The value $\Delta E_{light*}$ was calculated from the values of L*a*b* according to the following equation:

$$\Delta E_{light*} = \Delta E_{Lab}* \text{ non-irradiated lock} - \Delta E_{Lab}* \text{ irradiated lock}$$

The lower the value of $\Delta E_{light*}$, the better the light-fastness.

| Coupler | Base | Comparative support Recital ®: | | | | Support of the invention (A1) + (B1) + (C1) | | | |
|---|---|---|---|---|---|---|---|---|---|
| | | L* | a* | b* | $\Delta E_{Lab}*$ | L* | a* | b* | $\Delta E_{Lab}*$ |
| 2,7-Dihydroxynaphthalene | para-Phenylene diamine | 22.98 | 3.42 | 3.15 | 36.79 | 20.06 | 4.73 | 3.19 | 39.67 |
| 2-Naphthol | 4-(3-Aminopyrazolo[1,5-a]pyridin-2-yl)-1,1-dimethylpiperazin-1-ium chloride hydrochloride | 50.70 | −17.03 | 18.49 | 19.65 | 38.2 | −17.31 | 17.08 | 26.89 |

It is seen, unexpectedly, that the composition according to the invention affords much greater colour build-up $\Delta E_{Lab}*$ on 90% grey hair and thus better colour coverage at the root than that obtained with a prior art composition.

Light-Fastness

| Coupler | Base | Suntest (hours) | L* (D65) | a* (D65) | b* (D65) | $\Delta E_{Lab}*$ | $\Delta E_{light}*$ |
|---|---|---|---|---|---|---|---|
| 4-Methoxy-2-naphthol | 4-(3-Aminopyrazolo[1,5-a]pyridin-2-yl)-1,1-dimethylpiperazin-1-ium chloride hydrochloride | 0 | 34.28 | −3.87 | 0.09 | 27.98 | 1.2 |
| | | 18 | 34.83 | −3 | 1.3 | 26.78 | |
| 6-methoxy-2-naphthol | 4-(3-Aminopyrazolo[1,5-a]pyridin-2-yl)-1,1-dimethylpiperazin-1-ium chloride hydrochloride | 0 | 36.53 | −17.54 | 17.55 | 28.34 | 1.0 |
| | | 18 | 38.09 | −18.33 | 18.87 | 27.34 | |
| 2-Naphthol | 4-(3-Aminopyrazolo[1,5-a]pyridin-2-yl)-1,1-dimethylpiperazin-1-ium chloride hydrochloride | 0 | 38.2 | −17.31 | 17.08 | 26.89 | −0.24 |
| | | 18 | 39.96 | −18.6 | −17.87 | 26.65 | |

It is found that the colorations obtained with the compositions of the invention show very good light-fastness.

Example 2

With a Coupler d) Derived from the Phenols of Formula (B1)

The following compositions are prepared, in which the amounts are expressed in grams of active materials.

Composition A2

| Ingredients | A2 |
|---|---|
| Liquid petroleum jelly | 64.5 |
| 2-Octyldodecanol | 11.5 |
| Distearyldimethylammonium-modified hectorite | 3 |
| Propylene carbonate | 1 |
| Oxyethylenated sorbitan monolaurate (4 OE) | 11 |
| Glycol distearate | 8 |
| Oxyethylenated lauryl alcohol (2 OE) | 1 |

Composition B2

| Ingredients | B2 |
|---|---|
| Propylene glycol | 6.2 |
| Ethyl alcohol | 8.25 |
| Hexylene glycol (2-methyl-2,4-pentanediol) | 3 |
| Dipropylene glycol | 3 |
| Monoethanolamine | 14.5 |
| Sodium metabisulfite | 0.7 |
| Vitamin C: L-ascorbic acid | 0.25 |
| Diethylenetriaminepentaacetic acid, pentasodium salt as a 40% aqueous solution | 1 |
| Hydroxyethylcellulose (Natrosol 250 HHR, Aqualon) | 3.5 |
| Oxidation base | $2 \times 10^{-2}$ mol |
| Coupler | $2 \times 10^{2}$ mol |
| Water | qs 100 g |

Composition C2 (Oxidizing Agent)

| Ingredients | C2 |
|---|---|
| Cetylstearyl alcohol (Nafol 1618F) | 8 |
| Glycerol | 0.5 |

-continued

| Ingredients | C2 |
|---|---|
| Liquid petroleum jelly | 20 |
| Oxyethylenated cetylstearyl alcohol (33 OE) | 3 |
| Oxyethylenated rapeseed acid amide (4 OE) | 1.2 |
| Tetrasodium pyrophosphate | 0.03 |
| Diethylenetriaminepentaacetic acid, pentasodium salt as a 40% aqueous solution | 0.15 |
| Phosphoric acid | 0.1 |
| Tetramethylhexamethylenediamine/1,3-dichloropropylene polycondensate (aqueous 40% solution) | 0.1 |
| Polydimethyldiallylammonium chloride (aqueous 40% solution) | 0.2 |
| 50% aqueous hydrogen peroxide solution | 6 |
| Sodium stannate | 0.04 |
| Vitamin E | 0.1 |
| Phosphoric acid | qs pH 2.2 |
| Water | qs 100 g |

At the time of use, the following are mixed together (on a weight basis):

10 parts of composition A2
4 parts of composition B2
16 parts of composition C2

The mixture obtained is then applied to locks of natural hair containing 90% white hairs.

The bath ratio "mixture/lock" is, respectively, 10/1 (g/g).

The leave-on time is 30 minutes at 27° C.

After this time, the locks are rinsed, and then washed with shampoo and dried.

Calculation of the Colour Variation ($\Delta E_{ab}^*$)

The colour build-up ($\Delta E_{ab}^*$) was evaluated in the CIE L* a* b* system. In this L*, a*, b* system, L* represents the intensity of the colour, a* indicates the green/red colour axis and b* the blue/yellow colour axis. The lower the value of L*, the darker or more intense the colour.

The value of $\Delta E_{ab}^*$ was calculated from the values of L*a*b* according to equation (i) below:

$$\Delta E_{ab}^* = \sqrt{(L^*-L_o^*)^2 + (a^*-a_o^*)^2 + (b^*-b_o^*)^2} \quad (i)$$

The colour build-up ($\Delta E_{Lab}^*$) was calculated on locks of untreated hair ($L_o^*$, $a_o^*$ and $b_o^*$) and on locks of dyed hair (L*, a* and b*). The L*, a*, b* values for the untreated Natural Grey (NG) hair are as follows L*=57.93, a*=0.76, b*=14.32.

The greater the value of $\Delta E_{ab}^*$, the better the coverage of the treated fibres and thus of the roots.

Results

| Base | Coupler | L | a | b | $\Delta E_{ab}^*$ |
|---|---|---|---|---|---|
| 2-[(3-Aminopyrazolo[1,5-a]pyridin-2-yl)oxy]ethanol hydrochloride | 2-Acetamidophenol | 20.3 | 7.87 | −9.84 | 45.28 |

Strong coloration of natural hair containing 90% white hairs is observed, which reflects good build-up at the root, i.e. good coverage of the roots.

Example 3

With an Acylaminophenol-Based Coupler d)

The following compositions are prepared, in which the amounts are expressed in grams of active materials.

Composition A3

| Ingredients | A3 |
|---|---|
| Liquid petroleum jelly | 64.5 |
| 2-Octyldodecanol | 11.5 |
| Distearyldimethylammonium-modified hectorite | 3 |
| Propylene carbonate | 1 |
| Oxyethylenated sorbitan monolaurate (4 OE) | 11 |
| Glycol distearate | 8 |
| Oxyethylenated lauryl alcohol (2 OE) | 1 |

Composition B3

| Ingredients | B3 |
|---|---|
| Propylene glycol | 6.2 |
| Ethyl alcohol | 8.25 |
| Hexylene glycol (2-methyl-2,4 pentanediol) | 3 |
| Dipropylene glycol | 3 |
| Monoethanolamine | 14.5 |
| Sodium metabisulfite | 0.7 |
| Vitamin C: L-ascorbic acid | 0.25 |
| Diethylenetriaminepentaacetic acid, pentasodium salt as a 40% aqueous solution | 1 |
| Hydroxyethylcellulose (Natrosol 250 HHR, Aqualon) | 3.5 |
| Oxidation base | $2 \times 10^{-2}$ mol |
| Coupler | $2 \times 10^{-2}$ mol |
| Water | qs 100 g |

Composition C3 (Oxidizing Agent)

| Ingredients | C3 |
|---|---|
| Cetylstearyl alcohol (Nafol 1618F) | 8 |
| Glycerol | 0.5 |
| Liquid petroleum jelly | 20 |
| Oxyethylenated cetylstearyl alcohol (33 OE) | 3 |
| Oxyethylenated rapeseed acid amide (4 OE) | 1.2 |
| Tetrasodium pyrophosphate | 0.03 |
| Diethylenetriaminepentaacetic acid, pentasodium salt as a 40% aqueous solution | 0.15 |
| Phosphoric acid | 0.1 |
| Tetramethylhexamethylenediamine/1,3-dichloropropylene polycondensate (aqueous 40% solution) | 0.1 |
| Polydimethyldiallylammonium chloride (aqueous 40% solution) | 0.2 |
| 50% aqueous hydrogen peroxide solution | 6 |
| Sodium stannate | 0.04 |
| Vitamin E | 0.1 |
| Phosphoric acid | qs pH 2.2 |
| Water | qs 100 g |

At the time of use, the following are mixed together (on a weight basis):

10 parts of composition A3
4 parts of composition B3
16 parts of composition C3

The mixture obtained is then applied to locks of natural hair containing 90% white hairs.

The "mixture/lock" bath ratio is 10/1 (g/g).

The leave-on time is 30 minutes at 27° C.

After this time, the locks are rinsed, and then washed with shampoo and dried.

Calculation of the Colour Variation ($\Delta E_{ab}^*$)

The colour build-up ($\Delta E_{ab}^*$) was evaluated in the CIE L* a* b* system. In this L*, a*, b* system, L* represents the intensity of the colour, a* indicates the green/red colour axis and b* the blue/yellow colour axis. The lower the value of L*, the darker or more intense the colour.

The value of $\Delta E_{ab}^*$ was calculated from the values of $L^*a^*b^*$ according to equation (i) below:

$$\Delta E_{ab}^* = \sqrt{(L^*-L_o^*)^2+(a^*-a_o^*)^2+(b^*-b_o^*)^2} \quad (i)$$

The colour build-up ($\Delta E_{Lab}^*$) was calculated on locks of untreated hair ($L_o^*$, $a_o^*$ and $b_o^*$) and on locks of dyed hair ($L^*$, $a^*$ and $b^*$). The $L^*$, $a^*$, $b^*$ values for the untreated Natural Grey (NG) hair are as follows V=57.93, a*=0.76, b*=14.32.

The greater the value of $\Delta E_{ab}^*$, the better the coverage of the treated fibres and thus of the roots.

Calculation of the Light-Fastness
- machine: Suntest XLS+ (from Atlas) equipped with an infrared quartz filter and a special UV filter, xenon arc lamp (2200 W)
- principle: the locks are fixed onto card supports, one half of the lock being obscured with a card. The sample holders are placed in the machine on horizontal plates arranged under a lamp, for 18 hours.

The light-fastness is evaluated by determining the $DE_{light}^*$.

The value of $DE_{light}^*$ was calculated from the values of $L^*a^*b^*$ according to following equation:

$$DE_{light}^* = \Delta E_{ab}^* \text{non-irradiated lock} - \Delta E_{ab}^* \text{ irradiated lock}$$

The lower the value of $DE_{light}^*$, the better the light-fastness.

Results

| Coupler | Base | Suntest (h) | L* (D65) | a* (D65) | b* (D65) | $\Delta E_{ab}^*$ | $DE_{light}^*$ |
|---|---|---|---|---|---|---|---|
| (structure) | 4-(3-Aminopyrazolo[1,5-a]pyridin-2-yl)-1,1-dimethylpiperazin-1-ium chloride hydrochloride | 0 | 28.32 | −3.14 | −16.27 | 42.75 | 0.74 |
| | | 18 | 26.23 | −3.43 | −12.93 | 42.01 | |
| | 2-Methyl-4-N-methyl-N-β-(hydroxyethylamino) aniline sulfate | 0 | 35.99 | −16.32 | −13.56 | 39.37 | 1.27 |
| | | 18 | 32.08 | −12.88 | −10.12 | 38.1 | |
| | 4-N,N-Bis(β-hydroxyethylamino) aniline sulfate monohydrate | 0 | 24.93 | −3.22 | −14.81 | 44.2 | −0.51 |
| | | 18 | 24.41 | −3.86 | −14.89 | 44.71 | |

Strong build-up on natural grey hair is observed, which reflects excellent coverage of the roots. The light-fastness is moreover excellent.

Example 4

With an Acylaminophenol-Based Coupler d)

The process described in Example 1 above is performed, using the coupler/base combination in the table below. The dyeing results are collated in the table below:

| Coupler | Base | L | a | b | $\Delta E_{ab}^*$ |
|---|---|---|---|---|---|
| (structure) | 4-N,N-Bis(β-hydroxyethylamino)-aniline sulfate monohydrate | 29.93 | −5.62 | 1.36 | 31.5 |

Strong build-up on natural grey hair is observed, which reflects excellent coverage of the roots.

Example 5

With a Quinoline-Based Coupler d)

The following compositions are prepared, in which the amounts are expressed in grams of active materials.

Composition A5:

| Ingredients | A5 |
|---|---|
| Liquid petroleum jelly (fatty substance) | 64.5 |
| 2-Octyldodecanol (fatty substance) | 11.5 |
| Distearyldimethylammonium-modified hectorite | 3 |
| Propylene carbonate | 1 |
| Oxyethylenated sorbitan monolaurate (4 OE) (surfactant) | 11 |
| Glycol distearate | 8 |
| Oxyethylenated lauryl alcohol (2 OE) (surfactant) | 1 |

Composition B5:

| Ingredients | B5 |
|---|---|
| Propylene glycol | 6.2 |
| Ethyl alcohol | 8.25 |
| Hexylene glycol (2-methyl-2,4 pentanediol) | 3 |
| Dipropylene glycol | 3 |
| Monoethanolamine (basifying agent) | 14.5 |
| Sodium metabisulfite | 0.7 |
| Vitamin C: L-ascorbic acid | 0.25 |
| Diethylenetriaminepentaacetic acid, pentasodium salt as a 40% aqueous solution | 1 |

-continued

| Ingredients | B5 |
|---|---|
| Hydroxyethylcellulose (Natrosol 250 HHR, Aqualon) | 3.5 |
| Oxidation base | $2 \times 10^{-2}$ mol |
| Coupler | $2 \times 10^{-2}$ mol |
| Water | qs 100 g |

Composition C1 (Chemical Oxidizing Agent):

| Ingredients | C5 |
|---|---|
| Cetylstearyl alcohol (Nafol 1618F) (fatty substance) | 8 |
| Glycerol | 0.5 |
| Liquid petroleum jelly (fatty substance) | 20 |
| Oxyethylenated cetylstearyl alcohol (33 OE) (surfactant) | 3 |
| Oxyethylenated rapeseed acid amide (4 OE) (surfactant) | 1.2 |
| Tetrasodium pyrophosphate | 0.03 |
| Diethylenetriaminepentaacetic acid, pentasodium salt as a 40% aqueous solution | 0.15 |
| Phosphoric acid | 0.1 |
| Tetramethylhexamethylenediamine/1,3-dichloro-propylene polycondensate (aqueous 40% solution) | 0.1 |
| Polydimethyldiallylammonium chloride (aqueous 40% solution) | 0.2 |
| Hydrogen peroxide as an aqueous 50% solution (chemical oxidizing agent) | 6 |
| Sodium stannate | 0.04 |

The mixture obtained is then applied to hair that is 90% grey (NG). The "mixture/lock" bath ratio is 10/1 (g/g). The leave-on time is 30 minutes at 27° C.

After this time, the locks are rinsed, and then washed with shampoo and dried.

The results obtained with the composition of the invention were compared with those obtained with a prior art composition (Recital®) containing in the mixture with the oxidizing agent the same dyes at the same concentrations.

Calculation of the Colour Variation ($\Delta E_{Lab}^*$)

The colour build-up ($\Delta E_{Lab}^*$) was evaluated in the CIE L* a* b* system. In this L*, a*, b* system, L* represents the intensity of the colour, a* indicates the green/red colour axis and b* the blue/yellow colour axis. The lower the value of L*, the darker or more intense the colour.

The value of $\Delta E_{Lab}^*$ was calculated from the values of L*a*b* according to equation (i) below:

$$\Delta E_{Lab}^* = \sqrt{(L^*-L_o^*)^2+(a^*-a_o^*)^2+(b^*-b_o^*)^2} \quad (i)$$

The colour build-up ($\Delta E_{Lab}^*$) was calculated on locks of untreated hair ($L_o^*$, $a_o^*$ and $b_o^*$) and on locks of dyed hair (L*, a* and b*). The L*, a*, b* values for the untreated Natural Grey (NG) hair are as follows V=57.93, a*=−0.76, b*=14.32.

The greater the value of $\Delta E_{Lab}^*$, the better the coverage of the treated fibres and thus of the roots.

| | | Comparative support Recital ®: | | | | Support of the invention (A5) + (B5) + (C5) | | | |
|---|---|---|---|---|---|---|---|---|---|
| Coupler | Base | L | a | b | $\Delta E_{Lab}^*$ | L | a | b | $\Delta E_{Lab}^*$ |
| 8-Hydroxyquinoline sulfate | 4-(3-Aminopyrazolo[1,5-a]pyridin-2-yl)-1,1-dimethylpiperazin-1-ium chloride hydrochloride | 39.03 | −10.99 | −6.14 | 30.23 | 28.95 | −10.21 | −8.43 | 38.44 |
| 5-Hydroxyquinoline | 4-(3-Aminopyrazolo[1,5-a]pyridin-2-yl)-1,1-dimethylpiperazin-1-ium chloride hydrochloride | 46.87 | −9.33 | 1.4 | 19.78 | 40.98 | −11.89 | −4.96 | 28.62 |
| 7-Hydroxyquinoline | 2-[(3-Aminopyrazolo[1,5-a]pyridin-2-yl)oxy]ethanol hydrochloride | 42.56 | 3.48 | 17.01 | 15.83 | 34.57 | 4.54 | 22.54 | 25.05 |

-continued

| Ingredients | C5 |
|---|---|
| Vitamin E | 0.1 |
| Phosphoric acid | qs pH 2.2 |
| Water | qs 100 g |

At the time of use, the following are mixed together (on a weight basis):
10 parts of composition A5
4 parts of composition B5
16 parts of composition C5

It is seen, unexpectedly, that the composition according to the invention affords much greater colour build-up $\Delta E_{Lab}^*$ on 90% grey hair and thus better colour coverage at the root than that obtained with a prior art composition.

The invention claimed is:

1. A composition for dyeing keratin fibers, comprising:
   a) at least one fatty substance;
   b) at least one surfactant;

c) at least one oxidation base;
d) at least one coupler chosen from:
  ii) phenols of formula (B1) below:

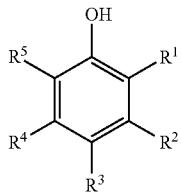

(B1)

and also salts thereof, optical and geometrical isomers and tautomers thereof, and hydrates thereof;
in which formula (B1):
  $R^1$, $R^2$, $R^3$, $R^4$ and $R^5$, which may be identical or different, are chosen from:
    hydrogen;
    halogen atoms;
    optionally substituted, linear or branched $C_1$-$C_8$ alkyl and $C_3$-$C_8$ alkenyl radicals;
    —SR and —OR groups in which R is chosen from hydrogen and optionally substituted, linear or branched $C_1$-$C_8$ alkyl and $C_3$-$C_8$ alkenyl radicals;
    ($C_1$-$C_4$)alkylcarbonyl groups;
    hydrogenocarbonyl groups (H—C(O)—);
    sulfonic acid groups;
    group —NH—C(O)—R' and —NH—S(O)$_2$R' groups in which R' is chosen from hydrogen, optionally substituted, linear or branched $C_1$-$C_8$ alkyl and $C_3$-$C_8$ alkenyl radicals, and optionally substituted phenyl groups;
  at least one of the radicals $R^1$, $R^3$ and $R^5$ is a hydrogen atom;
  two groups chosen from $R^1$, $R^2$, $R^3$, $R^4$ and $R^5$ and borne by adjacent carbon atoms may form, together with said carbon atoms, an optionally substituted ring or heterocycle, optionally interrupted with at least one group comprising at least one heteroatom chosen from oxygen, sulfur, carbonyl groups, and —NR"— groups in which R" is chosen from hydrogen and $C_1$-$C_4$ alkyl and ($C_1$-$C_4$)alkylcarbonyl radicals;
  the phenols of formula (B1) comprise only one group —NH—C(O)— and/or at least one group —NH—S(O)$_2$—, these groups being optionally engaged in a heterocycle;
  iii) acylaminophenols of formula (B2) below, salts thereof, optical and geometrical isomers and tautomers thereof, and hydrates thereof:

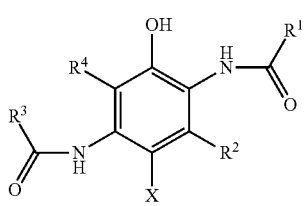

(B2)

in which formula (B2):
  $R^1$, $R^2$, $R^3$ and $R^4$, which may be identical or different, are chosen from linear or branched, saturated or unsaturated $C_1$-$C_{10}$ hydrocarbon-based chains, wherein at least one carbon atom may be replaced with an entity chosen from oxygen, nitrogen, sulfur and S(O)$_2$, wherein at least one carbon atom may be substituted with at least one halogen atom, and wherein the hydrocarbon-based chain, when it comprises from 4 to 10 carbon atoms, possibly forms one or more 3- to 8-membered rings;
  $R^2$ may be a hydrogen atom;
  $R^4$ may be chosen from —OR and —NR$_2$ groups in which R, which may be identical or different, is chosen from hydrogen and $C_1$-$C_4$ alkyl radicals; and
  X is chosen from hydrogen, halogen atoms, $C_1$-$C_4$ alkoxy radicals and phenoxy radicals, which are optionally substituted and
  iv) quinolines of formulae (B'1) and (B'2), and also salts thereof, optical and geometrical isomers and tautomers thereof, and hydrates thereof:

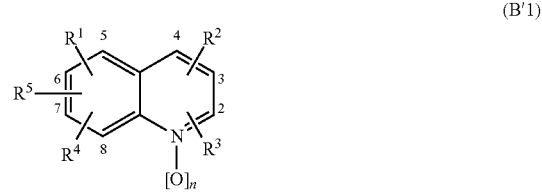

(B'1)

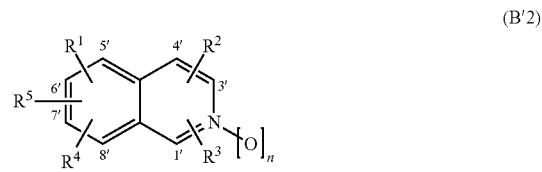

(B'2)

in which formulae (B'1) and (B'2):
  $R^1$ is chosen from hydroxyl and amino groups;
  $R^2$, $R^3$, $R^4$ and $R^5$, which may be identical or different, are chosen from:
    i) hydrogen;
    ii) halogen atoms;
    iii) hydroxyl;
    iv) NR$^a$R$^b$, wherein R$^a$ and R$^b$, which may be identical or different, are chosen from hydrogen and ($C_1$-$C_8$)alkyl groups optionally substituted with a hydroxyl group or a (di)($C_1$-$C_8$)(alkyl)amino group;
    or alternatively R$^a$ and R$^b$, with the nitrogen atom, together form a saturated or partially unsaturated 3- to 10-membered mono- or polycyclic heterocycle comprising from 1 to 5 heteroatoms chosen from oxygen, nitrogen, sulfur, sulfoxide S(O) and sulfone S(O)$_2$, the heterocycle optionally being substituted with a ($C_1$-$C_4$)alkyl group or an oxo group;
    v) ($C_1$-$C_8$)alkyl optionally substituted with at least one entity chosen from halogen atoms and hydroxyl and amino NR$^a$R$^b$ group as defined previously;
    vi) ($C_1$-$C_8$)alkoxy;
    vii) ($C_1$-$C_8$)alkyl-S(O)$_p$— with p=0, 1 or 2; and
    viii) aryloxy;
  or alternatively two contiguous radicals $R^2$ and $R^3$ form, together with the carbon atoms to which each is attached, a (hetero)cycle or a (hetero)aryl optionally substituted with a) a halogen atom, b) a hydroxyl, c) an amino group NR$^a$R$^b$ as defined previously, d) ($C_1$-$C_8$)alkyl optionally substituted with at least one entity chosen from halogen atoms and hydroxyl and amino NR$^a$R$^b$ groups as defined previously, e) (C$_1$-C$_8$) alkoxy, or f) (C$_1$-C$_8$)alkyl-S(O)$_p$— with p=0, 1 or 2;
n is 0;
e) at least one basifying agent; and
f) optionally at least one chemical oxidizing agent;
wherein the at least one fatty substance is present in the composition in a total amount of at least 25% by weight relative to the total weight of the composition.

2. The composition according to claim 1, wherein the at least one fatty substance is chosen from C$_6$-C$_{16}$ alkanes, non-silicone oils of mineral, plant, animal or synthetic origin, fatty alcohols, fatty acid esters, fatty alcohol esters, non-silicone waxes and silicones.

3. The composition according to claim 1, wherein the at least one fatty substance is liquid at room temperature and at atmospheric pressure and is chosen from liquid petroleum jelly, C$_6$-C$_{16}$ alkanes, polydecenes, and esters of fatty acids or of fatty alcohols, which are liquid, and mixtures thereof.

4. The composition according to claim 1, wherein the at least one fatty substance is present in the composition in a total amount ranging from about 25% to about 80% by weight relative to the total weight of the composition.

5. The composition according to claim 1, further comprising at least one non-ionic surfactant.

6. The composition according to claim 5, wherein the non-ionic surfactant is chosen from mono- or polyoxyalkylenated and mono- or polyglycerolated nonionic surfactants.

7. The composition according to claim 1, wherein the at least one oxidation base is chosen from benzene-based oxidation bases and the addition salts thereof.

8. The composition according to claim 7, wherein the at least one oxidation base is chosen from para-phenylenediamines, bis(phenyl)alkylene-diamines, para-aminophenols and ortho-aminophenols, and the addition salts thereof.

9. The composition according to claim 1, wherein the at least one coupler is chosen from phenols of formula (B1) in which:
R$^1$, R$^2$, R$^3$, R$^4$ and R$^5$, which may be identical or different, are chosen from:
hydrogen;
chlorine;
linear or branched C$_1$-C$_8$ alkyl and C$_3$-C$_8$ alkenyl radicals, optionally substituted with at least one group chosen from hydroxyl, amino and carboxyl groups;
—OR groups in which R is chosen from hydrogen and linear or branched C$_1$-C$_4$ alkyl radicals;
—NH—C(O)—R' and —NH—S(O)$_2$R' groups in which R' is chosen from hydrogen, linear or branched C$_1$-C$_8$ alkyl radicals, and phenyl groups optionally substituted with at least one C$_1$-C$_4$ alkyl group,
at least one of the radicals R$^1$, R$^3$ and R$^5$ is a hydrogen atom;
two groups chosen from R$^1$, R$^2$, R$^3$, R$^4$ and R$^5$ and borne by adjacent carbon atoms may form, together with the said carbon atoms, a ring or heterocycle, optionally substituted with at least one C$_1$-C$_4$ alkyl group, optionally interrupted with at least one group chosen from oxygen, carbonyl groups, and —NR"— groups in which R" is chosen from hydrogen and C$_1$-C$_4$ alkyl and (C$_1$-C$_4$)alkylcarbonyl radicals;
the phenols of formula (B1) comprise only one group —NH—C(O)— and/or at least one group —NHSO$_2$—, these groups being optionally engaged in a heterocycle.

10. The composition according to claim 1, wherein the at least one coupler is chosen from an acylaminophenol couplers of formula (B2) in which:

R$^1$, R$^2$, R$^3$ and R$^4$, which may be identical or different, are chosen from linear or branched C$_1$-C$_{10}$ alkyl chains, wherein at least one of the carbon atoms may be replaced with an entity chosen from oxygen, nitrogen and sulfur atoms, SO$_2$, and NR groups wherein R is chosen from hydrogen and C$_1$-C$_4$ alkyl radicals, and wherein at least one carbon atom may be substituted with at least one halogen atom;

R$^2$ may be a hydrogen atom;

R$^4$ may be chosen from —OR and —NR$_2$ groups in which R, which may be identical or different, is chosen from hydrogen and C$_1$-C$_4$ alkyl radicals; and X is chosen from hydrogen, halogen atoms, C$_1$-C$_4$ alkoxy radicals and phenoxy radicals, which are optionally substituted.

11. The composition according to claim 1, wherein the at least one coupler is chosen from an acylaminophenol couplers of formula (B2) in which:
R$^1$, R$^3$ and R$^4$, which may be identical or different, are chosen from C$_1$-C$_4$ alkyl radicals;
R$^2$ is a hydrogen atom; and
R$^4$ may be chosen from —NHR groups in which R is chosen from C$_1$-C$_4$ alkyl radicals.

12. The composition according to claim 1, wherein the at least one coupler is chosen from quinolines of formulae (B'1) and (B'2) in which R$^2$, R$^3$, R$^4$ and R$^5$, which may be identical or different, are chosen from:
hydrogen;
halogen atoms;
hydroxyl;
(C$_1$-C$_6$)alkyl;
(poly)haloalkyl;
(di)(C$_1$-C$_6$)(alkyl)amino;
(di)(C$_1$-C$_6$)(alkyl)amino(C$_1$-C$_6$)(alkyl)amino; and
NR$^a$R$^b$ in which R$^a$ and R$^b$, with the nitrogen atom together form a saturated monocyclic 5- to 7-membered heterocycle comprising from 1 to 3 heteroatoms chosen from oxygen and nitrogen, the heterocycle possibly being substituted with a (C$_1$-C$_4$)alkyl group;
or alternatively two contiguous radicals R$^2$ and R$^3$ together form a benzo group.

13. The composition according to claim 1, wherein the at least one coupler is chosen from the compounds below, and also salts thereof, optical or geometrical isomers and tautomers thereof, and hydrates thereof:

acetaminophen/paracetamol
103-90-2

(11)

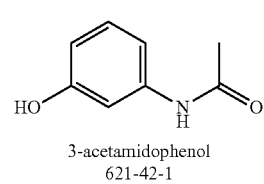

3-acetamidophenol
621-42-1

(12)

-continued

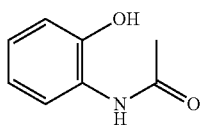
2-acetamidophenol
614-80-2
(13)

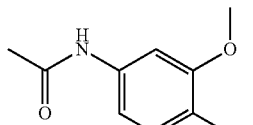
3-methoxyacetaminophenyl
3251-55-6
(14)

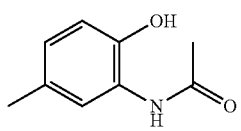
2-acetamido-4-methylphenol
6375-17-35 g
(15)

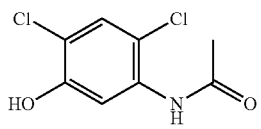
N-(2,4-dichloro-5-hydroxyphenyl)acetamide
67669-19-61 g
(16)

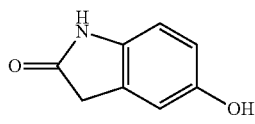
5-hydroxyoxindole
3416-18-0
(17)

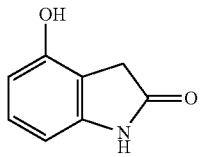
4-hydroxyoxindole
13402-55-6
(18)

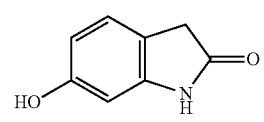
6-hydroxy-1,3-dihydroindol-2-one
(19)

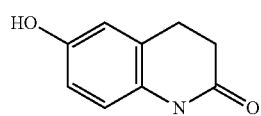
6-hydroxy-2-oxo-1,2,3,4-tetrahydroquinoline
54197-66-91 g
(20)

-continued

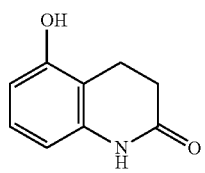
5-hydroxy-3,4-dihydro-2(1H)-quinolinone
30389-33-4
(21)

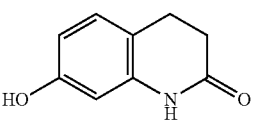
3,4-dihydro-7-hydroxy-2(1H)-quinolinone
22246-18-0
(22)

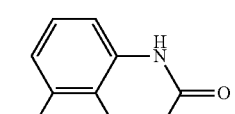
8-hydroxy-2H-benzo[b][1,4]oxazin-3(4H)-one
258532-76-2
(23)

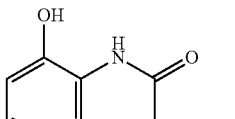
5-hydroxy-2H-1,4-benzoxazin-3(4H)-one
177210-33-2
(24)

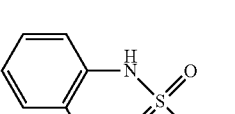
N-(2-hydroxyphenyl)-4-methylbenzenesulfonamide
3897-39-0
(25)

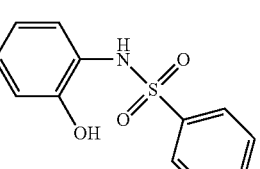
R0032598A
(26)

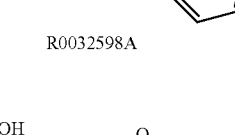
N-(2-hydroxyphenyl)methanesulfonamide
6912-38-5
(27)

(28)
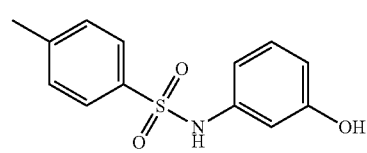
N-(3-hydroxyphenyl)-4-methylbenzenesulfonamide
3743-29-1

(31)
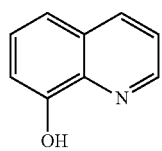
8-hydroxyquinoline:
148-24-3

(32)
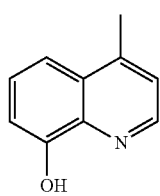
4-methyl-8-hydroxyquinoline:
3846-73-9

(33)
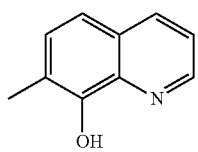
7-methyl-8-hydroxyquinoline:
5541-68-4

(34)
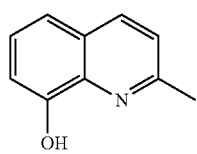
2-methyl-8-hydroxyquinoline:
826-81-3

(35)
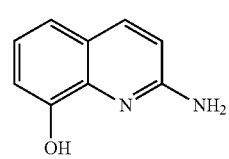
2-amino-8-hydroxyquinoline:
70125-16-5

(36)
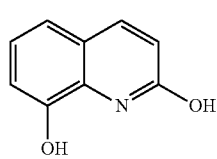
2,8-quinolinediol:
15450-76-7

(37)
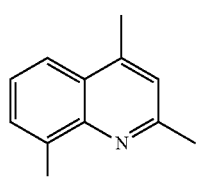
2,6-dimethyl-8-hydroxyquinoline:
115310-98-0

(38)
2-(methylamino)-8-quinolinol:
70125-17-6

(39)
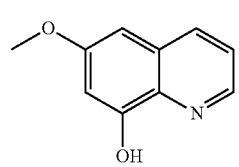
6-methoxy-8-quinolinol:
477601-28-8

(40)
2-methoxy-8-quinolinol:
74668-72-7

(41)
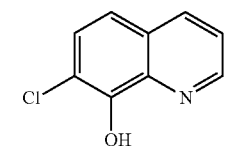
7-chloro-8-hydroxyquinoline:
876-86-8

(42)
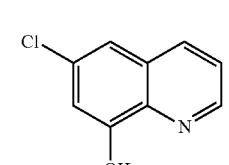
6-chloro-8-hydroxyquinoline:
18119-24-9

(43)
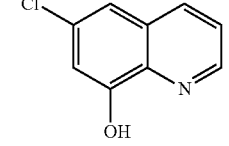
7-N-propyl-8-hydroxyquinoline:
58327-60-9

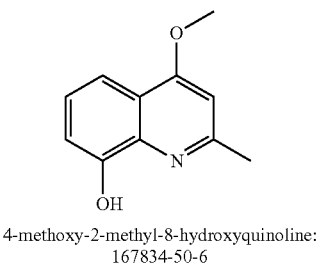
4-methoxy-2-methyl-8-hydroxyquinoline:
167834-50-6

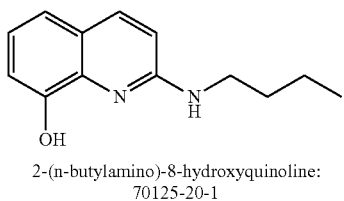
2-(n-butylamino)-8-hydroxyquinoline:
70125-20-1

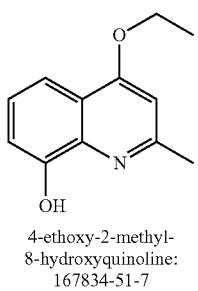
4-ethoxy-2-methyl-
8-hydroxyquinoline:
167834-51-7

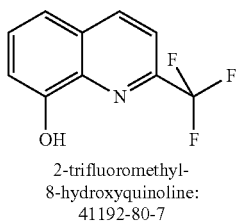
2-trifluoromethyl-
8-hydroxyquinoline:
41192-80-7

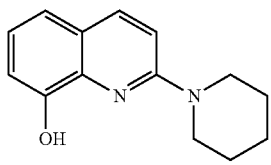
2-(1-piperidinyl)-8-
hydroxyquinoline:
31570-94-2

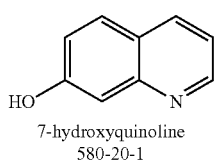
7-hydroxyquinoline
580-20-1

(44)

(45)

(46)

(47)

(48)

(49)

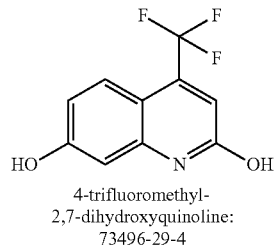
4-trifluoromethyl-
2,7-dihydroxyquinoline:
73496-29-4

2,7-dihydroxyquinoline:
70500-72-0

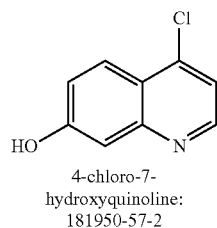
4-chloro-7-
hydroxyquinoline:
181950-57-2

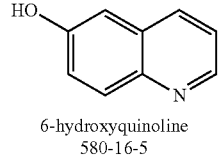
6-hydroxyquinoline
580-16-5

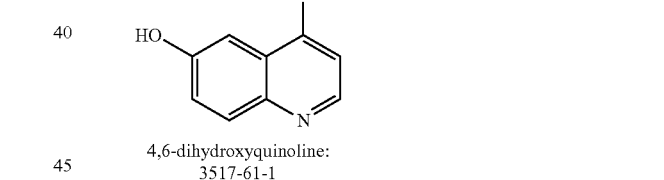
4,6-dihydroxyquinoline:
3517-61-1

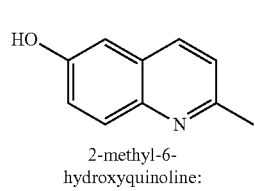
2-methyl-6-
hydroxyquinoline:
613-21-8

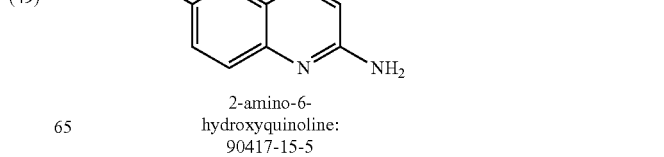
2-amino-6-
hydroxyquinoline:
90417-15-5

(50)

(51)

(52)

(53)

(54)

(55)

(56)

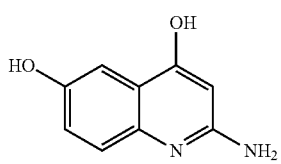
(57) 2-amino-4,6-dihydroxyquinoline:
42712-42-5
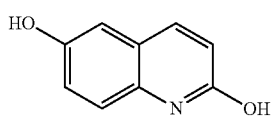
(58) 2,6-dihydroxyquinoline:
19315-93-6
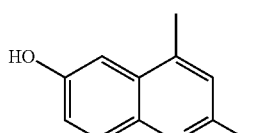
(59) 4-methyl-2,6-dihydroxyquinoline:
34982-01-9
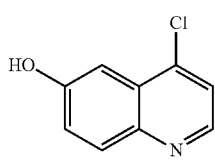
(60) 4-chloro-6-hydroxyquinoline:
148018-29-5
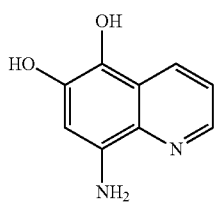
(61) 8-amino-5,6-dihydroxyquinoline:
17605-92-4
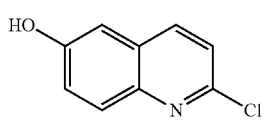
(62) 2-chloro-6-hydroxyquinoline:
577967-89-6
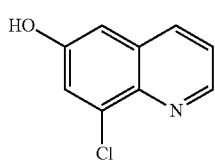
(63) 8-chloro-6-hydroxyquinoline:
18119-24-9
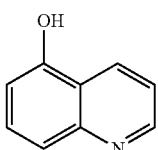
(64) 5-hydroxyquinoline:
578-67-6
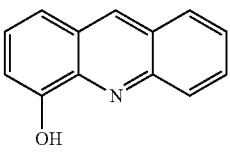
(65) 4-acridinol:
18123-20-1
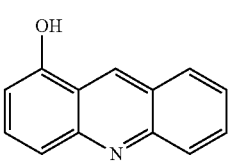
(66) 1-hydroxyacridine
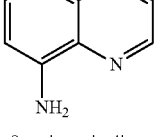
(67) 8-aminoquinoline:
23687-27-6
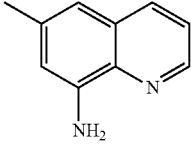
(68) 6-methyl-8-aminoquinoline:
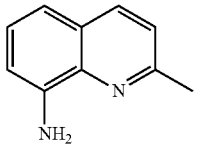
(69) 2-methyl-8-aminoquinoline: 18978-78-4
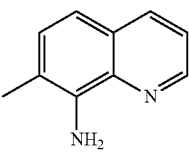
(70) 7-methyl-8-aminoquinoline: 5470-82-6

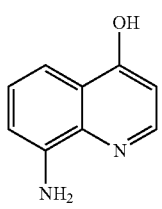
8-amino-4-hydroxyquinoline: 53867-95-1
(71)
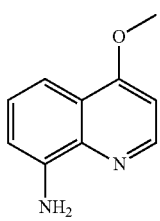
8-amino-4-methoxyquinoline: 59665-93-9
(72)
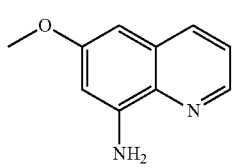
8-amino-6-methoxyquinoline: 90-52-8
(73)
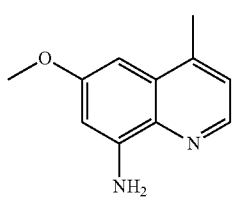
8-amino-6-methoxy-4-methylquinoline: 57514-21-3
(74)
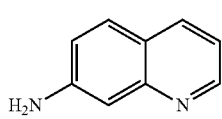
7-aminoquinoline: 580-19-8
(75)
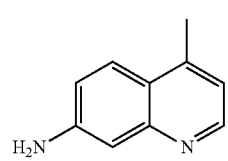
4-methyl-7-aminoquinoline: 114058-79-6
(76)
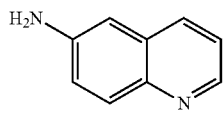
6-aminoquinoline: 580-15-4
(77)
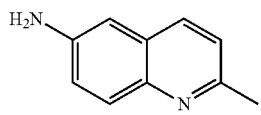
2-methyl-6-aminoquinoline: 65079-19-8
(78)
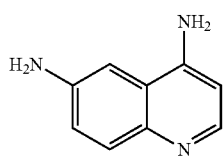
4,6-diaminoquinoline: 40107-09-3
(79)
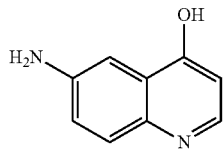
4-hydroxy-6-aminoquinoline
(80)
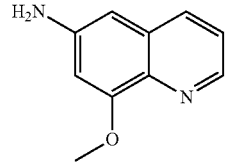
8-methoxy-6-aminoquinoline: 75959-08-9
(81)
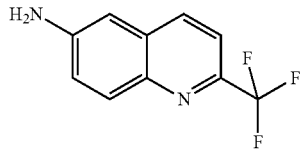
2-trifluoromethyl-6-aminoquinoline: 952182-53-5
(82)
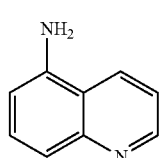
5-aminoquinoline: 611-34-7
(83)

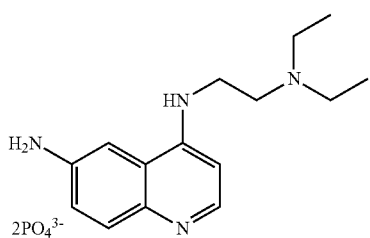

6-amino-4((2-(diethylamino)ethylamino)quinoline (diphosphate salt, 2PO₄³⁻) 78703-87-4 (84)

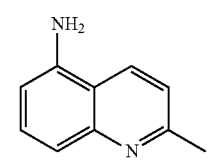

2-methyl-5-aminoquinoline: 54408-50-3 (85)

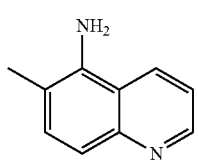

6-methyl-5-aminoquinoline: 50358-35-5 (86)

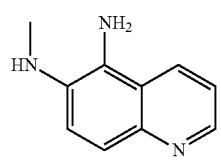

6-methyaminol-5-aminoquinoline: 14204-98-9 (87)

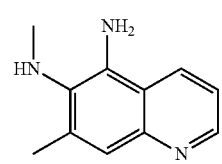

5-amino-6-methylaminol-7-methylquinoline: 83407-42-5 (88)

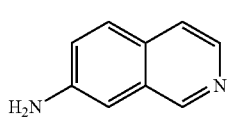

7-aminoisoquinoline: 23707-37-1 (89)

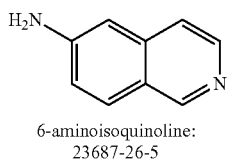

6-aminoisoquinoline: 23687-26-5 (90)

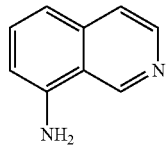

8-aminoisoquinoline: 23687-27-6 (91)

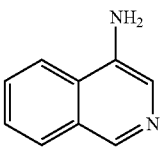

4-aminoisoquinoline: 23687-25-4 (92)

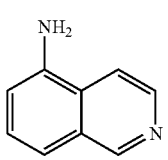

5-aminoisoquinoline: 1125-60-6 (93)

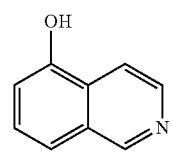

5-hydroxyisoquinoline: 2439-04-5 (94)

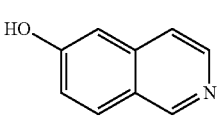

6-hydroxyisoquinoline: 7651-82-3 (95)

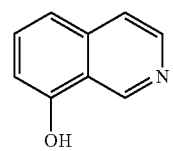

8-hydroxyisoquinoline: 3482-14-2 (96)

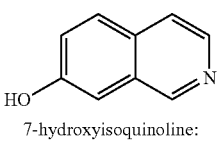

7-hydroxyisoquinoline: 7651-83-4 (97)

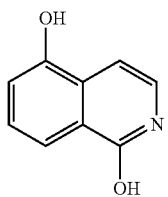

1,5-isoquinolinediol: 5154-5154-02-9.

14. The composition according to claim 1 further comprising at least one additional coupler chosen from meta-phenylenediamines, meta-aminophenols, meta-diphenols, naphthalene-based couplers, and heterocyclic couplers.

15. The composition according to claim 1, wherein the at least one basifying agent is chosen from mineral, organic and hybrid compounds.

16. The composition according to claim 15, wherein the at least one basifying agent is chosen from aqueous ammonia, alkali metal carbonates and bicarbonates, sodium hydroxide and potassium hydroxide, organic amines chosen from alkanolamines, oxyethylenated and/or oxypropylenated ethylenediamines, amino acids and the compounds of formula (I), and mixtures thereof:

wherein W is chosen from $C_1$-$C_6$ divalent alkylene radicals optionally substituted with at least one entity chosen from hydroxyl groups and $C_1$-$C_6$ alkyl radicals, and/or optionally interrupted with at least one heteroatom chosen from O and $NR_u$; and $R_x$, $R_y$, $R_z$, $R_t$ and $R_u$, which may be identical or different, are chosen from hydrogen and $C_1$-$C_6$ alkyl and $C_1$-$C_6$ hydroxyalkyl radicals and $C_1$-$C_6$ aminoalkyl radicals.

17. The composition according to claim 16, wherein the at least one basifying agent is chosen from alkanolamines and amino acids in neutral or ionic form.

18. The composition according to claim 1, further comprising at least one chemical oxidizing agent.

19. The composition according to claim 18, wherein the at least one chemical oxidizing agent is hydrogen peroxide.

20. A process for dyeing keratin fibers comprising applying to the fibers the composition according claim 1 in the presence of at least one chemical oxidizing agent.

21. The process according to claim 20, wherein the at least one chemical oxidizing agent is chosen from hydrogen peroxide.

22. The process according to claim 20, wherein the composition is obtained by mixing at least two compositions.

23. The process according to claim 22, wherein the composition is obtained by mixing two compositions:
composition (A) comprising:
  at least one oxidation base;
  at least one coupler chosen from ii) phenol-based couplers of formula (B1), iii) acylaminophenol couplers of formula (B2), and iv) quinoline-based couplers;
  at least one basifying agent; and
composition (B) comprising:
  at least one chemical oxidizing agent;
wherein at least one of the compositions (A) or (B) further comprises:
  at least one fatty substance; and
  at least one surfactant;
wherein the at least one fatty substance is present in the composition resulting from the mixing of compositions (A)+ (B) in a total amount of at least 25% by weight relative to the total weight of the composition.

24. The process according to claim 22, wherein the composition is obtained by mixing three compositions, wherein the three compositions are aqueous or wherein at least one of the three compositions is anhydrous.

25. The process according to claim 24, wherein the composition is obtained by mixing two aqueous compositions (B') and (C') and one anhydrous composition (A'), wherein:
anhydrous composition (A') comprises at least one fatty substance,
composition (B') comprises:
  at least one oxidation base; and
  at least one coupler chosen from ii) phenol-based couplers of formula (B1), iii) acylaminophenol couplers of formula (B2), and iv) quinoline-based couplers;
composition (C') comprises:
  at least one chemical oxidizing agent;
wherein at least one of compositions (A') and/or (B') comprises at least one basifying agent, and at least one of compositions (A'), (B') and/or (C') comprises at least one surfactant; and
wherein the at least one fatty substance is present in the composition resulting from the mixing of compositions (A')+ (B')+(C') in a total amount of at least 25% by weight relative to the total weight of the composition.

26. A multi-compartment device comprising a first compartment containing composition (A) as defined in claim 23 and at least a second compartment containing composition (B) as defined in claim 23, the compositions of the compartments being intended to be mixed together before application, to give a composition after mixing of (A)+(B), wherein the at least one fatty substance is present in a total amount of at least 25% by weight relative to the total weight of the composition derived from the mixing of (A)+(B).

27. A multi-compartment device comprising a first compartment containing composition (A') as defined in claim 25, a second compartment containing a cosmetic composition (B') as described in claim 25, and at least a third compartment containing composition (C') as described in claim 25; the compositions of the compartments being intended to be mixed together before application, to give a composition after mixing of (A')+(B')+(C'), wherein the at least one fatty substance is present in a total amount of at least 25% by weight relative to the total weight of the composition derived from the mixing of (A')+(B')+(C').

* * * * *